(12) United States Patent
Fortson

(10) Patent No.: US 12,232,721 B2
(45) Date of Patent: *Feb. 25, 2025

(54) METHODS, SYSTEMS, AND DEVICES FOR POSITIONING SUTURES FOR CLOSING AN OPENING IN TISSUE

(71) Applicant: Abbott Cardiovascular Systems, Inc., Santa Clara, CA (US)

(72) Inventor: Aaron M. Fortson, Fremont, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 120 days.

This patent is subject to a terminal disclaimer.

(21) Appl. No.: 17/751,956

(22) Filed: May 24, 2022

(65) Prior Publication Data
US 2022/0280150 A1 Sep. 8, 2022

Related U.S. Application Data

(63) Continuation of application No. 16/510,564, filed on Jul. 12, 2019, now Pat. No. 11,375,994.

(51) Int. Cl.
*A61B 17/04* (2006.01)
*A61B 17/06* (2006.01)

(52) U.S. Cl.
CPC ...... *A61B 17/0469* (2013.01); *A61B 17/0401* (2013.01); *A61B 17/0487* (2013.01);
(Continued)

(58) Field of Classification Search
CPC ............ A61B 17/0469; A61B 17/0487; A61B 2017/0409; A61B 2017/0414;
(Continued)

(56) References Cited

U.S. PATENT DOCUMENTS 3,328,876 A 7/1967 Hoppe
3,372,477 A 3/1968 Hoppe
(Continued)

FOREIGN PATENT DOCUMENTS

DE 9112301 1/1992
DE 9214580 4/1994
(Continued)

OTHER PUBLICATIONS

Office Action received for U.S. Appl. No. 10/004,817, mailed on Dec. 18, 2002.
(Continued)

*Primary Examiner* — Alexander J Orkin
(74) *Attorney, Agent, or Firm* — Workman Nydegger; Randy Shen

(57) ABSTRACT

A closure system for closing an opening in tissue, the closure system including a closure device and a knot replacement device configured to position a suture lock on a suture. The closure device includes a housing, a needle actuation handle cooperating with the housing, a first hollow needle selectively movable by the needle actuation handle and operatively cooperating with a suture anchor frictionally engaged with a slot and a lumen of the first hollow needle and coupled to a suture. A portion of the suture anchor rests along an outer surface of the first hollow needle as the first hollow needle is advanced through tissue adjacent the opening.

20 Claims, 19 Drawing Sheets

(52) U.S. Cl.
CPC ............... *A61B 2017/0409* (2013.01); *A61B 2017/0414* (2013.01); *A61B 2017/0417* (2013.01); *A61B 2017/0446* (2013.01); *A61B 2017/0472* (2013.01); *A61B 17/06004* (2013.01)

(58) Field of Classification Search
CPC .... A61B 2017/0417; A61B 2017/0446; A61B 2017/0472
See application file for complete search history.

(56) References Cited

U.S. PATENT DOCUMENTS

| | | | |
|---|---|---|---|
| 3,380,448 A | 4/1968 | Sadove et al. | |
| 3,625,556 A | 12/1971 | Stromberg | |
| 3,752,516 A | 8/1973 | Mumma | |
| 3,840,017 A | 10/1974 | Violante | |
| 4,235,238 A | 11/1980 | Ogiu et al. | |
| 4,246,698 A | 1/1981 | Lasner et al. | |
| 4,369,787 A | 1/1983 | Lasner et al. | |
| 4,423,837 A | 1/1984 | Clements | |
| 4,527,331 A | 7/1985 | Lasner et al. | |
| 4,602,635 A | 7/1986 | Mulhollan et al. | |
| 4,641,652 A | 2/1987 | Hutterer et al. | |
| 4,662,068 A | 5/1987 | Polonsky | |
| 4,841,888 A | 6/1989 | Mills et al. | |
| 4,845,851 A | 7/1989 | Warthen | |
| 4,957,498 A | 9/1990 | Caspari et al. | |
| 4,961,741 A | 10/1990 | Hayhurst | |
| 5,059,201 A | 10/1991 | Asnis | |
| 5,133,723 A | 7/1992 | Li et al. | |
| 5,176,691 A | 1/1993 | Pierce | |
| 5,176,695 A | 1/1993 | Dulebohn | |
| 5,242,427 A | 9/1993 | Bilweis | |
| 5,242,459 A | 9/1993 | Buelna | |
| 5,269,791 A | 12/1993 | Mayzels et al. | |
| 5,292,327 A | 3/1994 | Dodd et al. | |
| 5,304,190 A | 4/1994 | Reckelhoff et al. | |
| 5,312,423 A | 5/1994 | Rosenbluth et al. | |
| 5,342,459 A | 8/1994 | Klemp et al. | |
| 5,403,330 A | 4/1995 | Tuason | |
| 5,405,351 A | 4/1995 | Kinet et al. | |
| 5,405,354 A | 4/1995 | Sarrett | |
| 5,417,699 A | 5/1995 | Klein et al. | |
| 5,423,837 A | 6/1995 | Mericle et al. | |
| 5,462,562 A | 10/1995 | Elkus | |
| 5,520,702 A | 5/1996 | Sauer et al. | |
| 5,527,322 A | 6/1996 | Klein et al. | |
| 5,545,178 A | 8/1996 | Kensey et al. | |
| 5,549,617 A | 8/1996 | Green et al. | |
| 5,549,618 A | 8/1996 | Fleenor et al. | |
| 5,565,122 A | 10/1996 | Zinnbauer et al. | |
| 5,585,122 A | 12/1996 | Drum et al. | |
| 5,643,289 A | 7/1997 | Sauer et al. | |
| 5,649,939 A | 7/1997 | Reddick | |
| 5,662,681 A | 9/1997 | Nash et al. | |
| 5,669,917 A | 9/1997 | Sauer et al. | |
| 5,681,334 A | 10/1997 | Evans et al. | |
| 5,704,943 A | 1/1998 | Yoon et al. | |
| 5,746,752 A | 5/1998 | Burkhart | |
| 5,797,928 A | 8/1998 | Kogasaka | |
| 5,797,929 A | 8/1998 | Andreas et al. | |
| 5,830,234 A | 11/1998 | Wojciechowicz et al. | |
| 5,860,993 A | 1/1999 | Thompson et al. | |
| 5,879,371 A | 3/1999 | Gardiner et al. | |
| 5,997,555 A | 12/1999 | Kontos | |
| 6,004,295 A | 12/1999 | Langer et al. | |
| 6,007,544 A | 12/1999 | Kim | |
| 6,045,570 A | 4/2000 | Epstein et al. | |
| 6,051,004 A | 4/2000 | Gill | |
| 6,066,146 A | 5/2000 | Carroll et al. | |
| 6,077,277 A | 6/2000 | Mollenauer et al. | |
| 6,077,279 A | 6/2000 | Kontos | |
| 6,090,063 A | 7/2000 | Makower et al. | |
| 6,132,439 A | 10/2000 | Kontos | |
| 6,171,317 B1 | 1/2001 | Jackson et al. | |
| 6,206,895 B1 | 3/2001 | Levinson | |
| 6,254,620 B1 | 7/2001 | Koh et al. | |
| 6,261,272 B1 | 7/2001 | Gross et al. | |
| 6,488,690 B1 | 12/2002 | Morris et al. | |
| 6,527,785 B2 | 3/2003 | Sancoff et al. | |
| 6,620,185 B1 | 9/2003 | Harvie et al. | |
| 6,733,509 B2 | 5/2004 | Nobles et al. | |
| 6,746,457 B2 | 6/2004 | Dana et al. | |
| 6,860,890 B2 | 3/2005 | Bachman et al. | |
| 7,094,246 B2 | 8/2006 | Anderson et al. | |
| 7,147,646 B2 | 12/2006 | Dana et al. | |
| 7,632,287 B2 | 12/2009 | Baker et al. | |
| 7,651,509 B2* | 1/2010 | Bojarski | A61F 2/0811 606/232 |
| 7,842,051 B2 | 11/2010 | Dana et al. | |
| 7,918,867 B2 | 4/2011 | Dana et al. | |
| 7,992,571 B2 | 8/2011 | Gross et al. | |
| 8,197,497 B2 | 6/2012 | Nobles et al. | |
| 8,211,123 B2 | 7/2012 | Gross et al. | |
| 8,480,691 B2 | 7/2013 | Dana et al. | |
| 8,574,244 B2* | 11/2013 | Reynolds | A61B 17/0487 606/144 |
| 8,585,720 B2 | 11/2013 | Gross et al. | |
| 9,173,652 B2* | 11/2015 | Lombardo | A61B 17/0401 |
| 9,320,515 B2 | 4/2016 | Dana et al. | |
| 9,750,494 B2 | 9/2017 | Gross et al. | |
| 11,375,994 B2* | 7/2022 | Fortson | A61B 17/0487 |
| 2001/0044638 A1 | 11/2001 | Levinson et al. | |
| 2002/0019649 A1 | 2/2002 | Sikora et al. | |
| 2003/0236535 A1 | 12/2003 | Onuki et al. | |
| 2004/0249395 A1 | 12/2004 | Mikkaichi et al. | |
| 2005/0159762 A1* | 7/2005 | Nuutinen | A61B 17/06109 606/228 |
| 2005/0261710 A1* | 11/2005 | Sakamoto | A61B 17/0469 606/139 |
| 2006/0030884 A1 | 2/2006 | Yeung et al. | |
| 2007/0027476 A1* | 2/2007 | Harris | A61B 17/0469 606/232 |
| 2007/0073319 A1 | 3/2007 | Mikkaichi et al. | |
| 2007/0213587 A1 | 9/2007 | Moon | |
| 2008/0140092 A1* | 6/2008 | Stone | A61B 17/0469 606/139 |
| 2008/0208218 A1 | 8/2008 | Shiono | |
| 2008/0294001 A1 | 11/2008 | Surti | |
| 2009/0082797 A1 | 3/2009 | Fung et al. | |
| 2011/0046642 A1 | 2/2011 | Mcclurg et al. | |
| 2011/0172682 A1 | 7/2011 | Brady et al. | |
| 2013/0006277 A1* | 1/2013 | Stafford | A61B 17/0057 606/145 |
| 2013/0237997 A1* | 9/2013 | Arai | A61B 17/0401 606/232 |
| 2014/0194904 A1 | 7/2014 | Gross et al. | |
| 2015/0105805 A1* | 4/2015 | Fortson | A61B 17/0057 606/144 |
| 2015/0190129 A1* | 7/2015 | Nelson | A61B 17/0467 606/144 |
| 2015/0297213 A1 | 10/2015 | Azevedo et al. | |
| 2017/0020509 A1 | 1/2017 | Dana et al. | |
| 2017/0319197 A1 | 11/2017 | Gross et al. | |
| 2018/0344310 A1 | 12/2018 | Alfonso et al. | |

FOREIGN PATENT DOCUMENTS

| | | |
|---|---|---|
| EP | 0669103 | 9/1999 |
| EP | 00/69342 | 11/2000 |
| WO | 94/08515 | 4/1994 |
| WO | 95/32669 | 12/1995 |
| WO | 02/15795 | 2/2002 |
| WO | 03/049621 | 6/2003 |
| WO | 03/059174 | 7/2003 |

OTHER PUBLICATIONS

Notice of Allowance received for U.S. Appl. No. 10/004,817, mailed on Jul. 28, 2003.

(56) References Cited

OTHER PUBLICATIONS

Notice of Allowance received for U.S. Appl. No. 10/004,817, mailed on Feb. 4, 2004.
Office Action received for U.S. Appl. No. 10/027,681, mailed on Jun. 2, 2003.
Office Action received for U.S. Appl. No. 10/027,681, mailed on Dec. 8, 2003.
Office Action received for U.S. Appl. No. 10/027,681, mailed on May 28, 2004.
Office Action received for U.S. Appl. No. 10/027,681, mailed on Oct. 23, 2006.
Office Action received for U.S. Appl. No. 10/027,681, mailed on Apr. 17, 2007.
Office Action received for U.S. Appl. No. 10/027,681, mailed on Oct. 30, 2007.
Office Action received for U.S. Appl. No. 10/027,681, mailed on May 27, 2008.
Office Action received for U.S. Appl. No. 10/027,681, mailed on Dec. 23, 2008.
Office Action received for U.S. Appl. No. 10/027,681, mailed on Jul. 8, 2009.
Office Action received for U.S. Appl. No. 10/027,681, mailed on Feb. 17, 2010.
Office Action received for U.S. Appl. No. 10/027,681, mailed on Aug. 16, 2010.
Office Action received for U.S. Appl. No. 10/027,681, mailed on Jan. 19, 2011.
Office Action received for U.S. Appl. No. 10/027,681, mailed on Feb. 3, 2012.
Notice of Allowance received for U.S. Appl. No. 10/027,681, mailed on Apr. 5, 2012.
Office Action received for U.S. Appl. No. 10/324,730, mailed on Mar. 27, 2006.
Office Action received for U.S. Appl. No. 10/324,730, mailed on Aug. 08, 2006.
Office Action received for U.S. Appl. No. 10/324,730, mailed on Jan. 29, 2007.
Notice of Allowance received for U.S. Appl. No. 10/324,730, mailed on Aug. 30, 2007.
Office Action received for U.S. Appl. No. 10/324,730, mailed on Aug. 19, 2008.
Notice of Allowance received for U.S. Appl. No. 10/324,730, mailed on Oct. 30, 2009.
Notice of Allowance received for U.S. Appl. No. 10/324,730, mailed on Mar. 23, 2010.
Notice of Allowance received for U.S. Appl. No. 10/324,730, mailed on Sep. 22, 2010.
Office Action received for U.S. Appl. No. 10/661,155, mailed on Aug. 31, 2005.
Notice of Allowance received for U.S. Appl. No. 10/661,155, mailed on Feb. 23, 2006.
Office Action received for U.S. Appl. No. 10/860,443, mailed on May 17, 2006.
Notice of Allowance received for U.S. Appl. No. 10/860,443, mailed on Oct. 2, 2006.
Office Action received for U.S. Appl. No. 11/461,243, mailed on Apr. 29, 2009.
Office Action received for U.S. Appl. No. 11/461,243, mailed on Oct. 21, 2009.
Office Action received for U.S. Appl. No. 11/461,243, mailed on Mar. 15, 2010.
Notice of Allowance received for U.S. Appl. No. 11/461,243, mailed on Jul. 28, 2010.
Issue Notification received for U.S. Appl. No. 11/461,243, mailed on Nov. 10, 2010.
Office Action received for U.S. Appl. No. 11/465,035, mailed on Nov. 28, 2008.
Office Action received for U.S. Appl. No. 11/465,035, mailed on Mar. 4, 2010.
Office Action received for U.S. Appl. No. 11/465,035, mailed on Jun. 22, 2010.
Notice of Allowance received for U.S. Appl. No. 11/465,035, mailed on Nov. 19, 2011.
Office Action received for U.S. Appl. No. 12/914,658, mailed on Nov. 19, 2012.
Notice of Allowance received for U.S. Appl. No. 12/914,658, mailed on Mar. 7, 2013.
Office Action received for U.S. Appl. No. 13/539,095, mailed on Dec. 6, 2012.
Notice of Allowance received for U.S. Appl. No. 13/539,095, mailed on Jul. 10, 2013.
Office Action received for U.S. Appl. No. 13/936,593, mailed on Jul. 27, 2015.
Notice of Allowance received for U.S. Appl. No. 13/936,593, mailed on Jan. 12, 2016.
Office Action received for U.S. Appl. No. 14/083,173, mailed on Apr. 6, 2016.
Office Action received for U.S. Appl. No. 14/083,173, mailed on Oct. 18, 2016.
Notice of Allowance received for U.S. Appl. No. 14/083,173, mailed on Mar. 6, 2017.
Notice of Allowance received for U.S. Appl. No. 14/083,173, mailed on Jul. 3, 2017.
Office Action received for U.S. Appl. No. 15/137,547, mailed on Apr. 9, 2018.
Interview Summary received for U.S. Appl. No. 15/137,547, mailed on Jun. 5, 2018.
Notice of Allowance received for U.S. Appl. No. 15/137,547, mailed on Aug. 1, 2018.

* cited by examiner

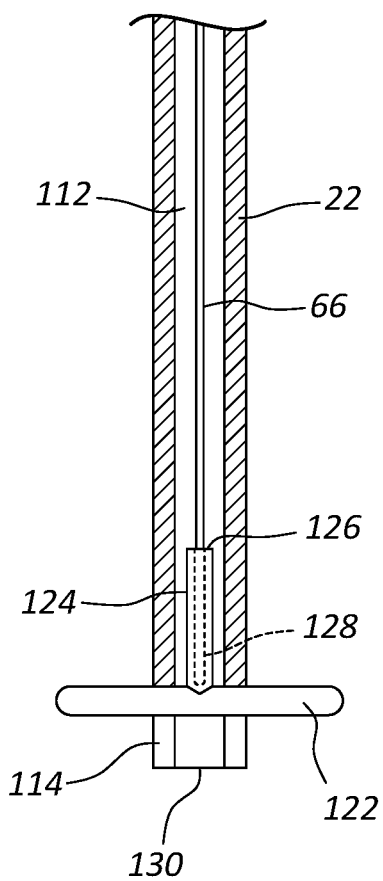
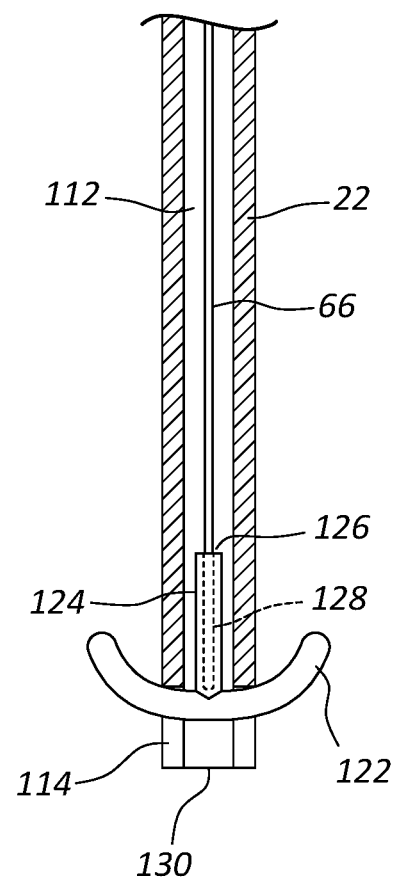
FIG. 9  FIG. 10

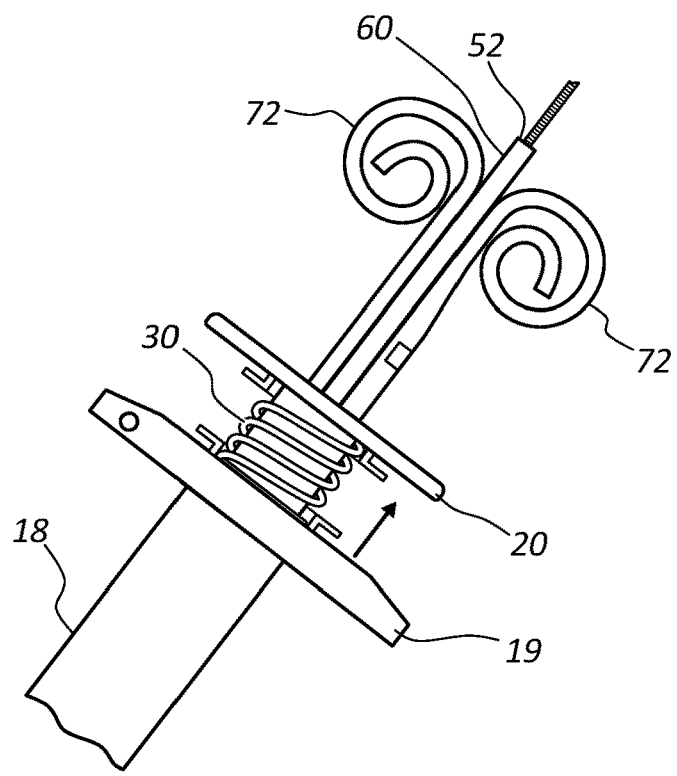
FIG. 17
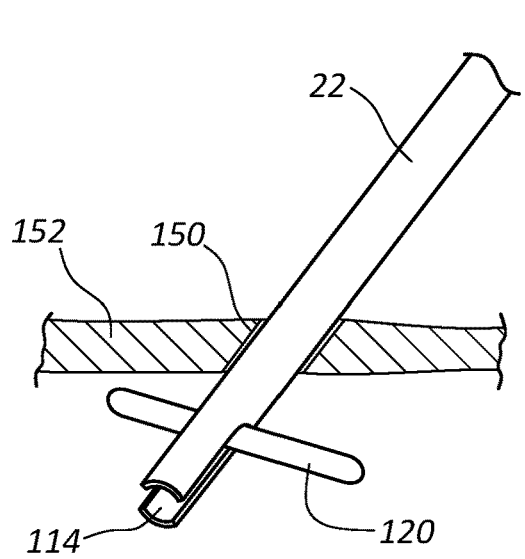 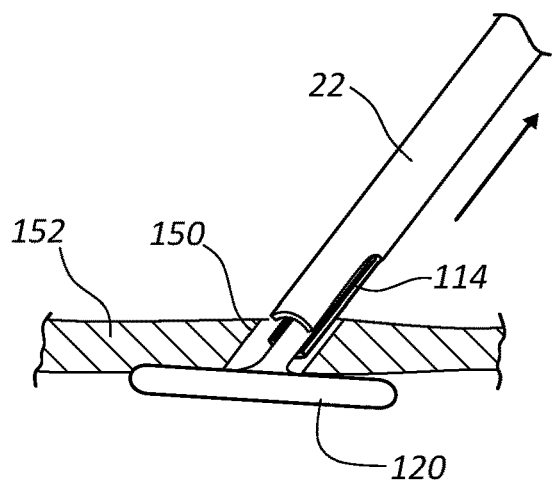
FIG. 18  FIG. 19

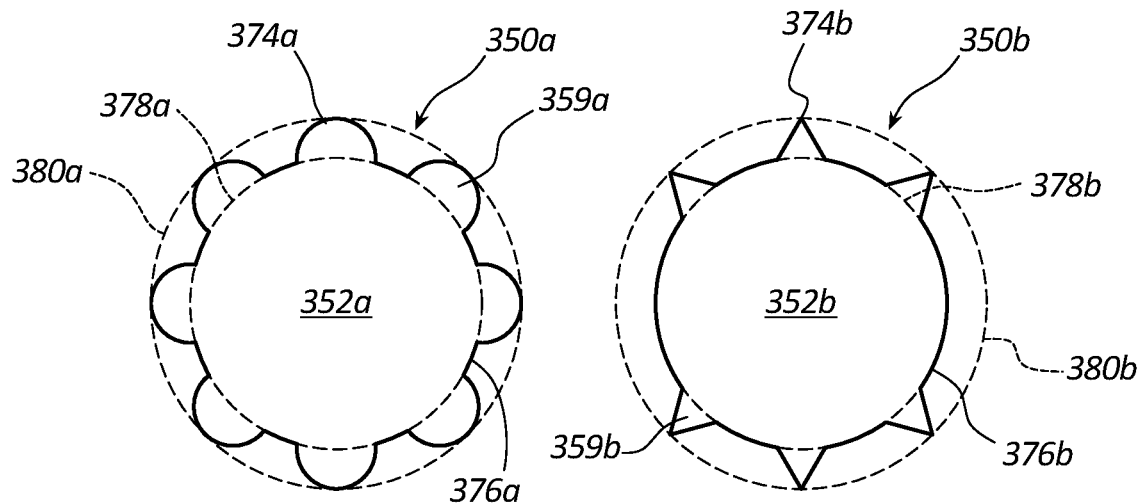
FIG. 33  FIG. 34
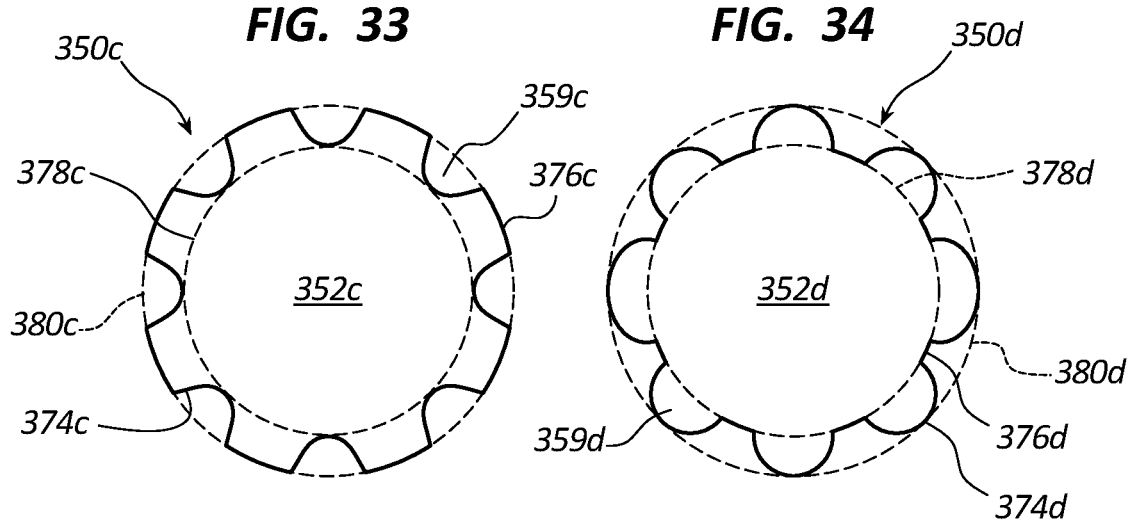
FIG. 35  FIG. 36
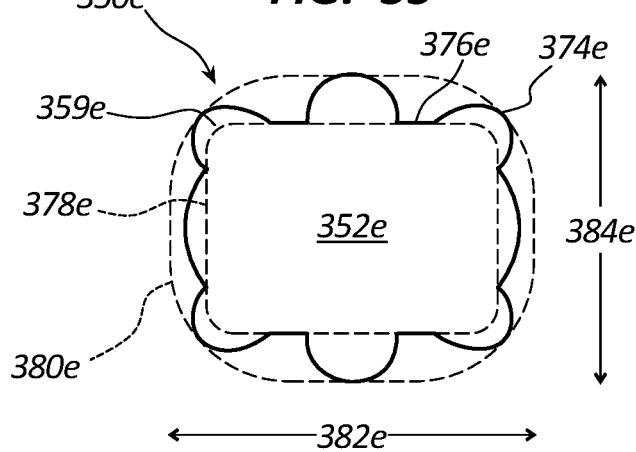
FIG. 37

METHODS, SYSTEMS, AND DEVICES FOR POSITIONING SUTURES FOR CLOSING AN OPENING IN TISSUE

CROSS-REFERENCE TO RELATED APPLICATIONS

This application is a continuation of U.S. patent application Ser. No. 16/510,564, filed Jul. 12, 2019, the entire contents of which are incorporated by reference herein.

BACKGROUND OF THE INVENTION

1. The Field of the Invention

The present disclosure relates generally to medical devices and their methods of use. In particular, the present disclosure relates to systems and devices for closing an opening in tissue and corresponding methods of use.

2. The Relevant Technology

A number of diagnostic and interventional vascular procedures are now performed transluminally, where a catheter is introduced to the vascular system at a convenient access location and guided through the vascular system to a target location using established techniques. Such procedures require vascular access which is usually established using the well-known Seldinger technique, as described, for example, in William Grossman's "Cardiac Catheterization and Angiography," 3rd Ed., Lea and Febiger, Philadelphia, 1986, incorporated herein by reference.

Upon completing the procedure, and vascular access is no longer needed, the devices and introducer sheath would be removed, leaving a puncture site in the vessel wall. Traditionally, external pressure would be applied to the puncture site until clotting and wound sealing occur; however, the patient must remain bedridden for a substantial period after clotting to ensure closure of the wound. This procedure may also be time consuming and expensive, requiring as much as an hour of a physician's or nurse's time. It is also uncomfortable for the patient and requires that the patient remain immobilized in the operating room, catheter lab, or holding area. In addition, a risk of hematoma exists from bleeding before hemostasis occurs. Although systems may be available to close the opening in tissue, such as a puncture providing access to the patient's vasculature, they provide limited control and flexibility to the operator, which may lead to improper or undesirable closure of the tissue opening, such as the puncture site.

BRIEF SUMMARY OF THE INVENTION

Various embodiments of a closure device for closing an opening in tissue are disclosed herein. Also disclosed are various embodiments methods for positioning, deploying, and removing the closure device associated with closing the opening.

In one configuration, a closure device for closing an opening in tissue includes a needle actuation handle cooperating with a housing, a hollow needle is selectively movable by the needle actuation handle, the needle including a slot extending proximally from a distal end of the needle, and a suture anchor positioned within and selectively releasable from the slot and coupled to a suture. A portion of the suture anchor extends proximally along an outer surface of the needle as the needle is advanced through tissue adjacent the opening.

In one configuration, the closure device includes a locking member selectively disposed about a body of a needle actuation handle distal a handle portion.

In one configuration, the closure device includes the needle actuation handle being biased proximally from the housing.

In one configuration, the closure device includes the suture anchor having two legs extending transversely to the suture in the pre-deployed state and a deployed state.

In one configuration, the closure device includes the suture anchor having two legs extending transversely to the suture in the pre-deployed state and a deployed state, the two legs extending proximally along the outer surface of the needle in the pre-deployed state.

In one configuration, the closure device for closing an opening in tissue includes a housing, a needle actuation handle cooperating with the housing, a hollow needle selectively movable by the needle actuation handle, the needle including a slot extending proximally from a distal end of the needle and communicating with a lumen of the hollow that is configured to receive a suture, and a suture anchor positioned within and selectively releasable from the slot and coupled to the suture. The suture anchor, at a position proximal the distal end of the needle, extends proximally along an outer surface of the needle as the needle is advanced through tissue adjacent the opening.

In one configuration, the closure device includes a suture storage receptacle disposed proximal a proximal end of a needle actuation handle, the suture extending from the distal end of the needle to the suture storage receptacle.

In one configuration, the closure device includes a suture storage receptacle that has a spiral form.

In one configuration, the closure device includes a distal end of the needle having a cutting edge.

In one configuration, the closure device includes a bleed back locator.

In one configuration, the closure device includes a locking member selectively disposed about a body of the needle actuation handle distal a handle portion.

In one configuration, the closure device includes a locking member having a locking channel receiving the body and a biasing member separating the handle portion and the housing.

In one configuration, the closure device includes a tether connecting the locking member to the housing.

In one configuration, the closure device includes a needle actuation handle and the needles are selectively slidable in both a proximal-to-distal direction and a distal-to-proximal direction, with the needle actuation handle and the needle being selectively removable from the housing.

In one configuration, the closure device includes a guidewire lumen ending from a proximal exit port towards a distal inlet port that is distal the distal end of the needle in the pre-deployed state.

In one configuration, a method is disclosed, the method including positioning a distal end of a closing device through a tissue opening, the closing device having a housing from which a needle is advanceable, advancing the needle from the housing towards tissue adjacent to the tissue opening, the needle having a slot accommodating a suture anchor and a lumen accommodating a suture, the suture anchor having two legs extending transversely from the anchor in a pre-deployed state and a deployed state, and advancing the needle through the tissue adjacent to the tissue opening, the two legs extending proximally along an outer surface of the needle as the needle is advanced through tissue adjacent the opening;

In one configuration, the method includes proximally retracting the needle following advancing the needle through the tissue to overcome engagement between the suture anchor and walls of the slot.

In one configuration, the method includes twisting the suture.

In one configuration, the method includes following twisting the suture, positioning a suture lock on the suture.

In one configuration, the method includes cutting the suture.

These and other objects and features of the present invention will become more fully apparent from the following description and appended claims or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 9 illustrates a cross-section view of a portion of a needle and suture anchor of the tissue opening closure device of FIG. 1 in a first position.

FIG. 10 illustrates a cross-section view of a portion of a needle and suture anchor of the tissue opening closure device of FIG. 1 in a second position.

FIGS. 11-21 illustrate a method for use of the tissue opening closure device so as to effect hemostasis.

FIG. 33 is a cross-sectional view of the alternate suture lock of FIG. 32 in accordance with the present invention.

FIG. 34 is a cross-sectional view of another alternate suture lock in accordance with the present invention.

FIG. 35 is a cross-sectional view of another alternate suture lock in accordance with the present invention.

FIG. 36 is a cross-sectional view of another alternate suture lock in accordance with the present invention.

FIG. 37 is a cross-sectional view of another alternate suture lock in accordance with the present invention.

DETAILED DESCRIPTION OF THE PREFERRED EMBODIMENTS

Figure 1:
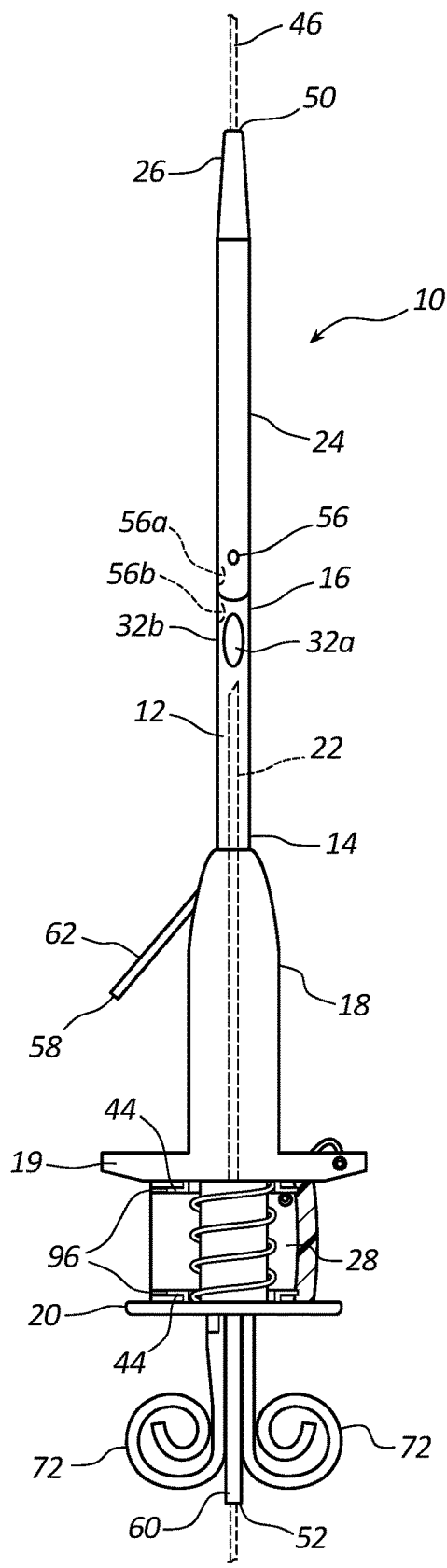
FIG. 1 illustrates a plan view of a tissue opening closure device according to an embodiment of the present invention.

The term "distal" as used herein, is a broad term and is used in its ordinary sense, including, without limitation, as in the direction of the patient, or away from a user of a device, or in a case of arterial deployment, in a direction of antegrade flow of blood. In the context of a medical device intervention with or through a vessel wall, "distal" herein refers to the interior or the lumen side of the vessel wall. In the context of a medical device intervention with or through an opening in tissue, "distal" herein refers to the interior side of the tissue.

The term "proximal" as used herein, is a broad term and is used in its ordinary sense, including, without limitation, as away from the patient, or toward the user, or in a case of arterial deployment, in a direction of retrograde flow of blood. In the context of a medical device intervention with or through a vessel wall, "proximal" herein refers to the exterior or outer side of the vessel wall. In the context of a medical device intervention with or through an opening in tissue, "proximal" herein refers to the exterior side of the tissue.

The term "hemostasis" as used herein, is a broad term and is used in its ordinary sense, including, without limitation, the arrest of bleeding or substantially blocking flow of blood outwardly from a vessel lumen while the vessel lumen is pressurized or sustaining physiological blood flow. This amount of blockage or occlusion to flow is further defined such that the blood loss which is experienced is less than an amount which would affect procedural methods or outcomes according to a physician user of a device of ordinary skill in the art. In other words, "hemostasis" is not intended to mean only "total hemostasis" such that there is a total lack of blood loss. Rather, the term is used to also mean "procedural hemostasis" as a relative term in its use among physicians of ordinary skill.

The term "suturing" as used herein, is a broad term and is used in its ordinary sense, including, without limitation, the process of joining two surfaces or edges together with a fastener so as to close an aperture, opening, or wound or join tissues. The fastener is usually a suture such as a thread of material (either polymeric or natural), gut, wire or the like. The term "fastener" as used herein, is a broad term and is used in its ordinary sense, including, without limitation, clamps, studs, hasps, catches, hooks, rivets, staples, snaps, stitches, VELCRO, buttons, and other coupling members.

The term "pre-close" as used herein, is a broad term and is used in its ordinary sense, including, without limitation, the placement of the sutures in a blood vessel, e.g., femoral artery, before the arteriotomy is enlarged by an endovascular sheath.

One or more specific embodiments of the present disclosure will be described below. In an effort to provide a concise description of these embodiments, some features of an actual embodiment may be described in the specification. It should be appreciated that in the development of any such actual embodiment, as in any engineering or design project, numerous embodiment-specific decisions will be made to achieve the developers' specific goals, such as compliance with system-related and business-related constraints, which may vary from one embodiment to another. It should further be appreciated that such a development effort might be complex and time consuming, but would nevertheless be a routine undertaking of design, fabrication, and manufacture for those of ordinary skill having the benefit of this disclosure.

The present disclosure relates to methods, systems, and devices for closing an opening in tissue, such as closing an opening or puncture through a wall of a body lumen. In one example embodiment, a closure system of the present disclosure may allow an operator to quickly and efficiently achieve hemostasis of an opening while simultaneously providing the operator with a greater measure of control and flexibility in positioning and anchoring portions of the closure system than previously available. For example, the closure system may allow an operator to achieve a more intimate securement of a closure element in the tissue, such as tissue surrounding a body lumen opening. In a yet further embodiment, the closure system may be compatible with a wider range of tissue structures and tissue thicknesses, such as body lumen wall thicknesses, thereby considering the possibility of calcifications or scar tissue. In addition, the closure system can optionally be configured to advance into a body lumen opening over a guidewire. In addition, the closure system can be used to pre-close the tissue opening. Furthermore, the closure system may be compatible with a variety of sizes of body lumen openings and tissue tracts.

Figure 2:
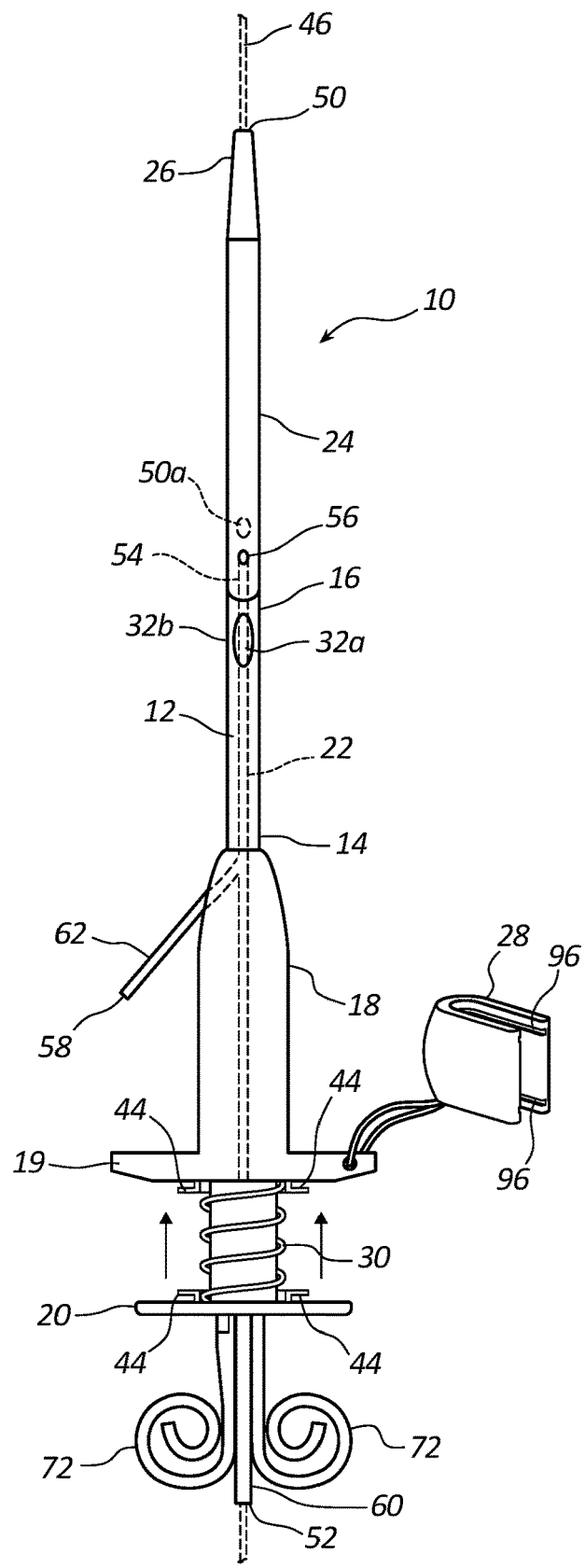
FIG. 2 illustrates the plan view of the tissue opening closure device of FIG. 1 within a detached locking member.
Figure 3:
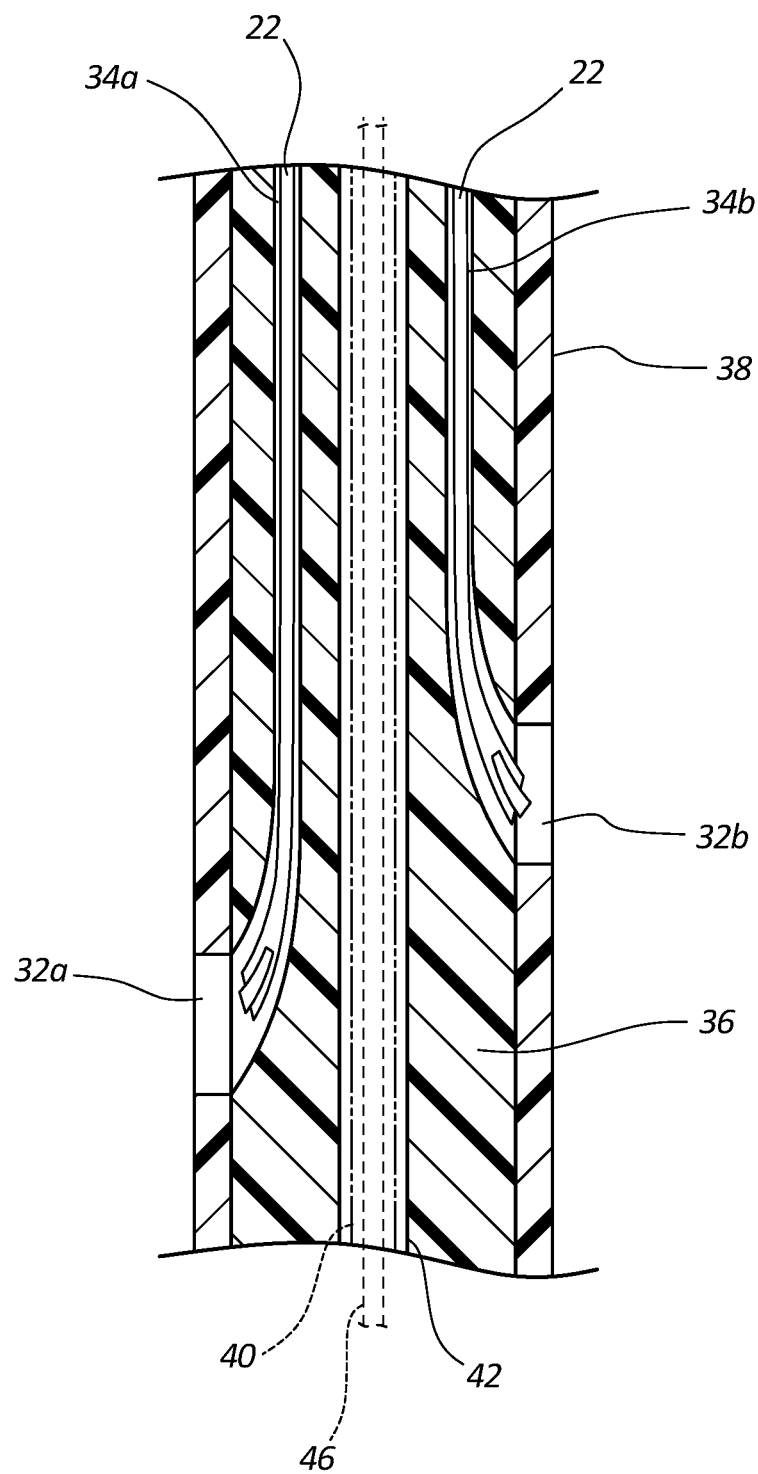
FIG. 3 illustrates a cross-section view of a portion of the tissue opening closure device of FIG. 1.

Referring now to FIG. 1, a closure device 10 generally has a shaft 12 having a proximal end 14 and a distal end 16. A proximal housing 18 supports a needle actuation handle 20 that is coupled to a plurality of needles 22 (FIG. 3) that can be advanced to penetrate tissue and deploy anchored sutures. A flexible, atraumatic guidebody 24, with an atraumatic tip 26, extends from the distal end 16 of the shaft 12. A lock member 28 is disposed between the proximal housing 18 and the needle actuation handle 20 to prevent inadvertent distal movement of the needle actuation handle 20 to deploy the plurality of needles 22, the lock member 28 being tethered to the proximal housing 18, such as to one of the finger grips 19. FIG. 1 illustrates the closure device 10 with the lock member 28 in a first position preventing the inadvertent distal movement before actuation and FIG. 2 illustrates the lock member 28 in a second position so that movement of the needle actuation handle 20 in the direction of the arrows advances the plurality of needles 22 (FIG. 3). A biasing member 30 is positioned relative to the needle actuation handle 20, such as on a portion of the needle actuation handle 20, to selectively maintain separation of the proximal housing 18 and the needle actuation handle 20. The biasing member 30 provides resistance to needle actuation handle 20 movement toward the proximal housing 18 and so provides enhanced control to the user. Additionally, the biasing member 30 aids in retracting the needles 22 delivering the self-locating suture anchor 120 (FIG. 8) of the suture. The anchor 120 will have an exposed portion so that when the user releases the needle actuation handle 20, the biasing member 30 will retract the needles 22 back through the vessel wall causing the exposed portion of the anchor 120 (FIG. 5) to engage with the vessel wall and pulled off the needle 22 as the needle 22 is retracted. Further details will be provided later.

As illustrated in FIGS. 1 and 3, disposed at the distal end 16 of the shaft 12 are needle ports 32a, 32b (anterior needle port 32a and posterior needle port 32b) to accommodate the plurality of needles 22 and through which the needles 22 would extend to penetrate tissue. The needle ports 32a, 32b communicate with needle lumens 34a, 34b, illustrated in the cross-sectional view of FIG. 3, which extend from the proximal housing 18 to the needle ports 32a, 32b. The needles 22 can be advanced distally to and through the needle ports 32a, 32b to penetrate tissue and also proximally to retrieve the needles 22.

Figure 4A:
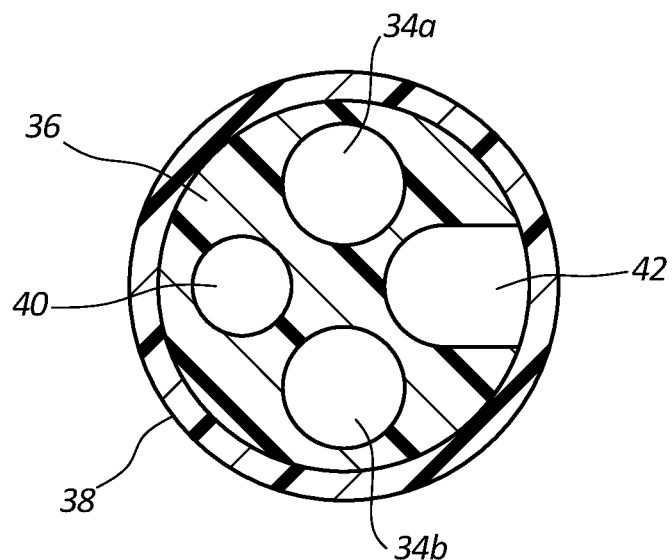
FIG. 4A illustrates another cross-sectional view of a portion of the tissue opening closure device of FIG. 1.

The needle lumens 34a, 34b are positioned in a body 36 of the shaft 12, the body 36 being covered with an outer sheath 38. As illustrated in FIGS. 3 and 4A, the needle lumens 34a, 34b are disposed on radially opposite sides of the body 36 with a guidewire lumen 40 and a marker lumen 42 being radially opposite each other at a location between the needle lumens 34a, 34b. Positioning the needle lumens 34a, 34b radially opposite each other positions the needles 22 on an anterior and posterior side of the shaft 12, consistent with anterior and posterior positioning of the needles 22 relative to the opening through which the shaft 12 is advanced. It will be understood that the needle lumens 34a, 34b, the guidewire lumen 40, and the marker lumen 42 and can be placed at other locations about the body 36, such as to achieve different needle puncture patterns, accommodate different target tissue within the patient's anatomy, or to vary a delivery procedure to position the closure device 10 in proximity to a tissue opening.

Figure 4B:
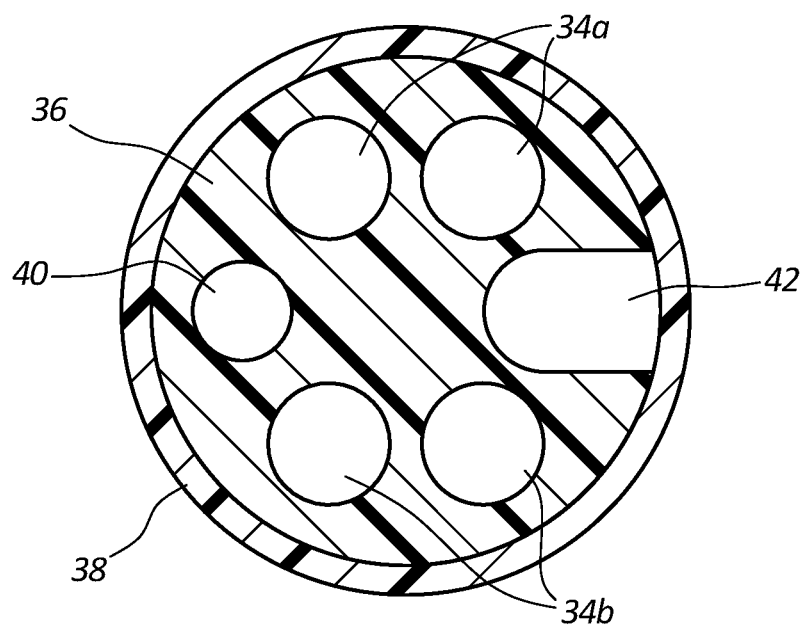
FIG. 4B illustrates an alternate cross-sectional view of a portion of the tissue opening closure device of FIG. 1.
Figure 4C:
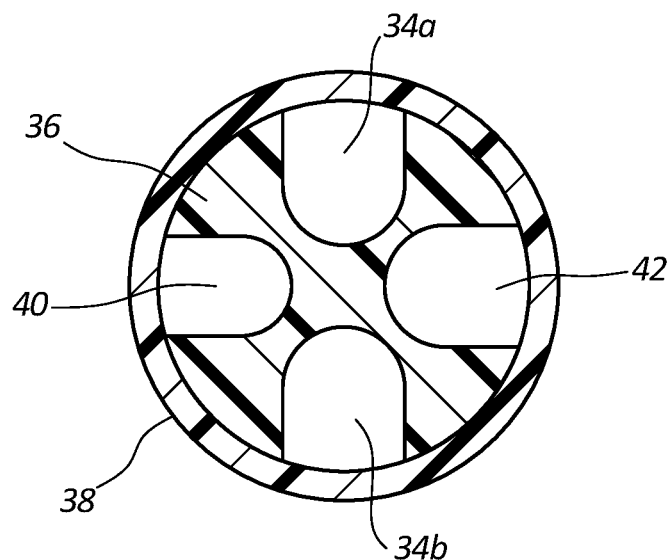
FIG. 4C illustrates an alternate cross-sectional view of a portion of the tissue opening closure device of FIG. 1.
Figure 4D:
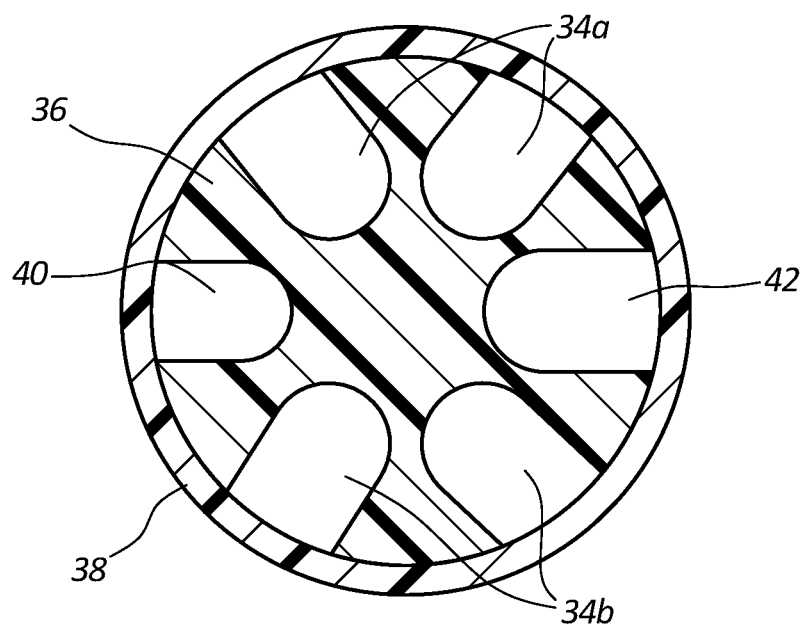
FIG. 4D illustrates an alternate cross-sectional view of a portion of the tissue opening closure device of FIG. 1.

FIGS. 4B-4D illustrate a number of alternate locations and forms for the needle lumens 34a, 34b and the guidewire lumen 40 within the body 36. For instance, FIG. 4B illustrates a plurality of needle lumens 34a, 34b radially opposite each other on the anterior and posterior sides of the shaft 12, with the guidewire lumen 40 radially spaced from the marker lumen 42. The needle lumens 34a, 34b and guidewire lumen 40 are lumens having generally circular cross-sections and are spaced from an outer periphery of the body 36. In contrast, the marker lumen 42 is illustrated as a through hole, groove, recess, or channel formed in the outer periphery of the body 36. That said, the marker lumen 42 can alternatively be a lumen having a generally cross-section and be spaced from the outer periphery of the body 36. Additionally, and as illustrated in FIGS. 4C-4D, the needle lumens 34a, 34b and guidewire lumen 40 can also take the form of a through-hole, groove, recess, or channel similar to the marker lumen 42 of FIGS. 4A-4B In addition to the illustrated alternate configurations, it will be understood that the needle lumens 34a, 34b can be disposed beside each other on one side, either anterior or posterior. Similarly, the guidewire lumen 40 and the marker lumen 42 can be disposed beside each other on one side, either anterior or posterior. The needle lumens 34a, 34b need not be separated by one or both of the guidewire lumen 40 and the marker lumen 42 in a circumferential direction about a longitudinal axis of the body 32.

Generally, the spacing of the needle lumens 34a, 34b or the spacing of the guidewire lumen 40 and the marker lumen 42 need not be about 180°. Instead, the spacing can be between about 5° to about 175° apart, between about 10° to about 165° apart, between about 20° to about 155° apart, between about 45° to about 135° apart. Additionally, while the needle lumens 34a, 34b, the guidewire lumen 40, and the marker lumen 42 can have a generally circular cross-section, alternate configurations are possible. For instance, the cross-sections of the lumens can be elliptical, oval, polygonal, non-circular, or combinations thereof.

The guidewire lumen 40 accommodates a guidewire 46 upon which the closure device 10 is advanced, whether by an over-the-wire or rapid exchange configuration. For instance, the guidewire lumen 40 can extend from an inlet port 50 at the atraumatic tip 26 to an exit port 52 positioned proximal the needle actuation handle 20 of the closure device 10. Alternatively, the guidewire lumen 40 can be formed on a small section of the guidebody 22 or the shaft 12, with both an input port 50 and an exit port 52 being formed in the guidebody 22 or the shaft 12. In still another configuration, the inlet port 50 can be disposed closer to the inlet 56 of the bleed back passageway 54, as shown in phantom in FIG. 2, as inlet 50a.

The marker lumen 42 forms part of a bleed back passageway 54 extending from the guidebody 24 to the proximal housing 18. When an inlet port 56 of the bleed back passageway 54 enters a body lumen, such as a blood vessel, the pressure of the blood will cause blood to flow through inlet port 56, along the passageway 54, and exit from the outlet port 58. Pulsating flow from the outlet port 58 indicates that the shaft 12 is appropriately positioned in the blood vessel. Instead of locating the inlet port 56 as illustrated in FIGS. 1 and 2, the inlet port can be disposed closer to the needle ports 32a, 32b, as illustrated in phantom in FIG. 1, as inlet ports 56a and 56b.

The needle lumens 34a, 34b, the guidewire lumen 40, and the marker lumen 42 can be formed from one or more tubes provided in the shaft 12, proximal housing 18, and the guidebody 24. For instance, as shown in FIGS. 1, 2, and 5, at least a portion of the guidewire lumen 40 is formed by the guidewire tube 60 extending from a proximal end of the needle actuation handle 20 and a guidewire tube 48 disposed within the guidebody 24, the guidewire tube 60 overlapping or being received within the guidewire tube 48 to form the guidewire lumen 40.

At least a portion of the marker lumen 42 is formed by the marker tube 62 extending from the proximal housing 18. Optionally, at least portions of the needle lumens 34a, 34b, the guidewire lumen 40, and the marker lumen 42 can be formed integrally with the body 36 of the shaft 12. For instance, the needle lumens 34a, 34b and the guidewire lumen 40 can be formed as the body 36 is extruded or otherwise formed. The marker lumen 42 can be partially formed in the body 36 when extruded and closed upon sealing by connecting the outer sheath 38 to the body 36. In still other configurations, the needle lumens 34a, 34b and the guidewire lumen 40 can be formed in a similar manner to the marker lumen 42, such as the needle lumens 34a, 34b and the guidewire lumen 40 being partially formed by the body 36 and closed or sealed when the outer sheath 38 connects to the body 36.

Figure 5:
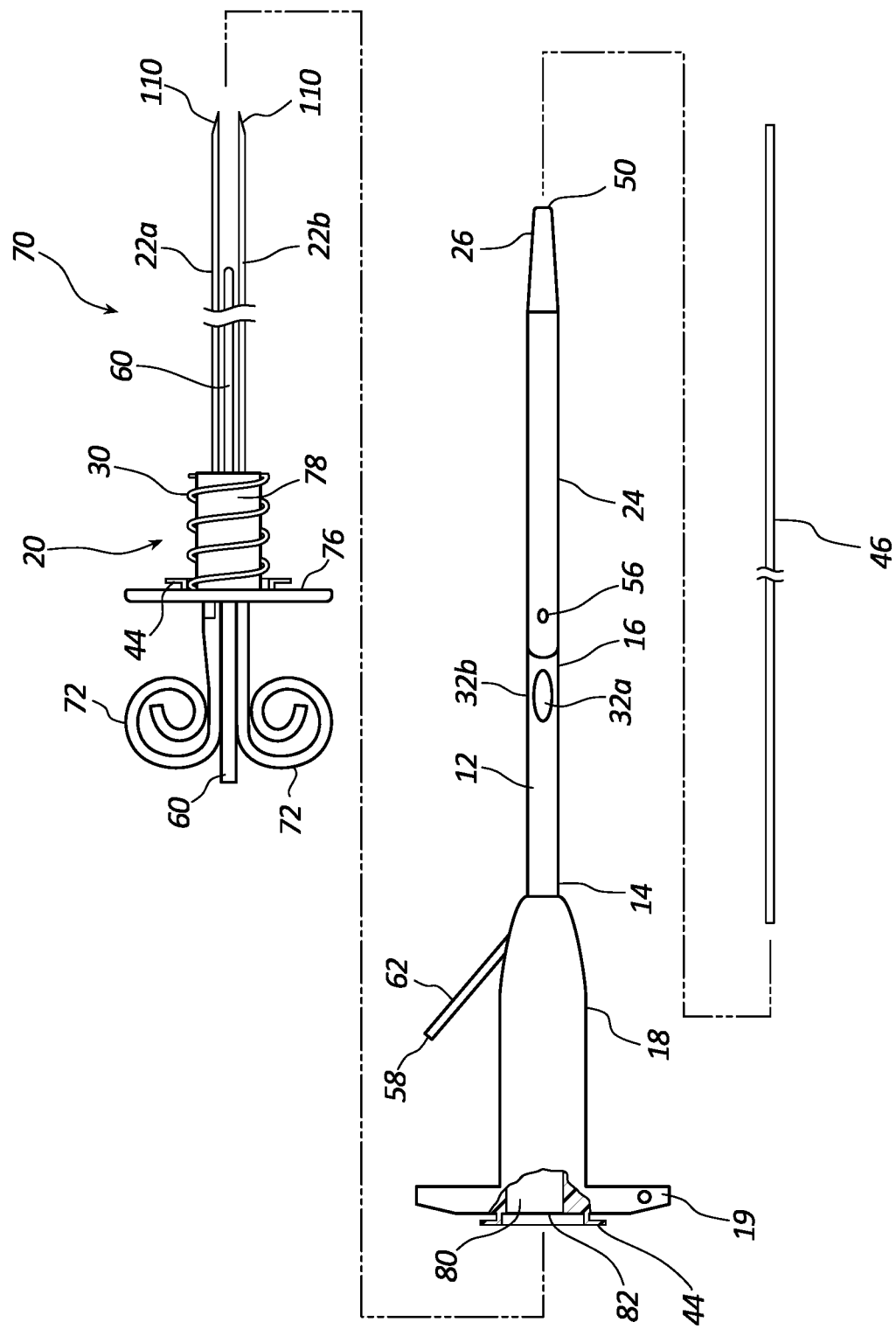
FIG. 5 illustrates an exploded view of the tissue opening closure device of FIG. 1.
Figure 6:
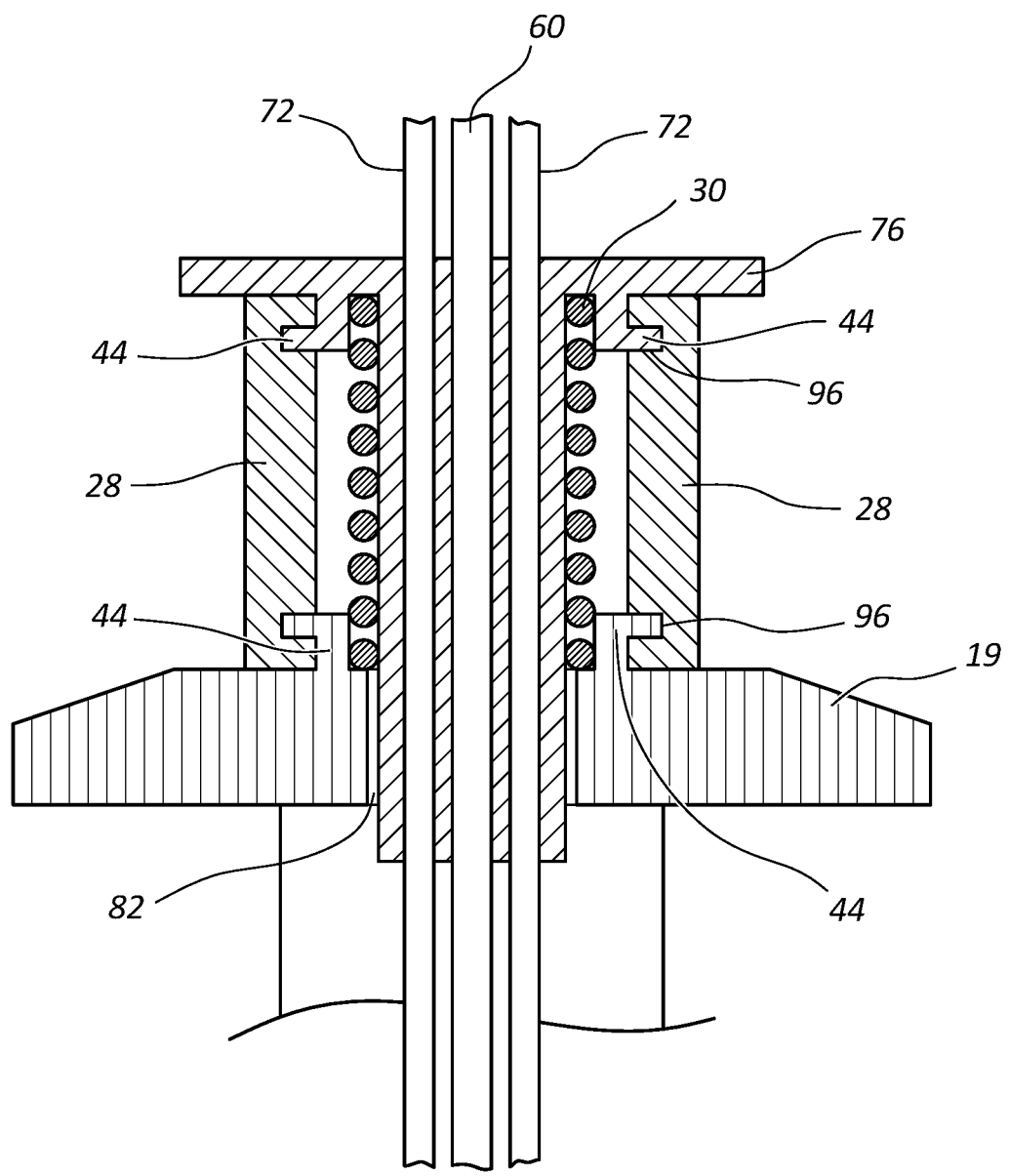
FIG. 6 illustrates a cross-sectional view of a portion of a needle actuation handle of the tissue opening closure device of FIG. 1.

Turning to FIGS. 5 and 6, the needles 22 and the needle actuation handle 20 form a needle assembly 70 that can be advanced into and retracted from the proximal housing 18. This movement not only moves the needle actuation handle 20 but also a suture storage receptacle 72, and optionally the guidewire tube 60, that extend from and are mounted to the needle actuation handle 20. When the needle assembly 70 is removed from the proximal housing 18, a suture 66 is released from the suture storage receptacle 72 as the suture storage receptacle 72 is slid over the suture. Similarly, the guidewire tube 60 is slid over the guidewire 46. Each length of suture 66 can be about 10.5 inches (26.7 cm) in length. Alternatively, the suture can have a length from about 10 inches (25.4 cm) to about 15 inches (38.1 cm) of working length from an engagement surface of the suture anchor 120 (FIG. 5).

To aid with such movement, a body portion 78 of the needle actuation handle 20 can be slidably received within an interior 80 of the proximal housing 18. With the plurality of the needles 22 being guided in their movement by the needle lumens 34a, 34b, the body portion 78 can simply slide within an opening 82 formed in the proximal housing 18. However, if additional control to the movement is desired, the body portion 78 and a portion of the proximal housing 18 can be keyed together so that rotational movement of the body portion 78 relative to the proximal housing 18, or vice versa, can be limited.

To further control movement of the needle actuation handle 20 into and away from the proximal using 18 in proximal-to-distal or distal-to-proximal directions, the biasing member 30 provides resistance to movement of the needle actuation handle 20 toward the proximal housing 18 and so provides enhanced control to the user. The biasing member 30, such as a spring, is positioned on the body portion 78 between a handle portion 76 of the needle actuation handle 20 and a proximal end of the proximal housing 18. As the biasing member 30 is compressed during proximal-to-distal movement of the handle portion 76, the biasing member 30 resists the movement. This provides enhanced tactile feel to the user, so needle penetration is more controlled. The biasing member 30 can have a generally uniform cross-section and approximates an outer diameter of the body portion 78. Alternatively, the biasing member 30 can have a configuration where it provides increased resistance as the proximal-to-distal translation of the handle portion 76 increases, i.e., the handle portion 76 moves closer to the proximal housing 18. This can be achieved, when the biasing member 30 is a spring, through increasing a diameter of the wires from the spring, changing a cross-section of the spring, or other manners know by those skilled in the art. It will also be appreciated that other biasing members can be used and may be adjusted to provide variable resistance. For instance, the spring force of the biasing member 30 may be linear or non-linear. The biasing member 30 can have a higher density of coils at a distal end and lower density of coils at a proximal end allowing for an increase in resistive force as the handle portion 76 is advanced. This would reduce a needle speed of the needles 22 at an end of the stroke of the handle portion 76 as the vessel is pierced by the needles 22. Additionally, detents (illustrated in phantom) could be provided at a proximal end and/or distal end of the body portion 78 to retain the biasing member 30 so it does not become disengaged from the body portion 78.

Figure 7:
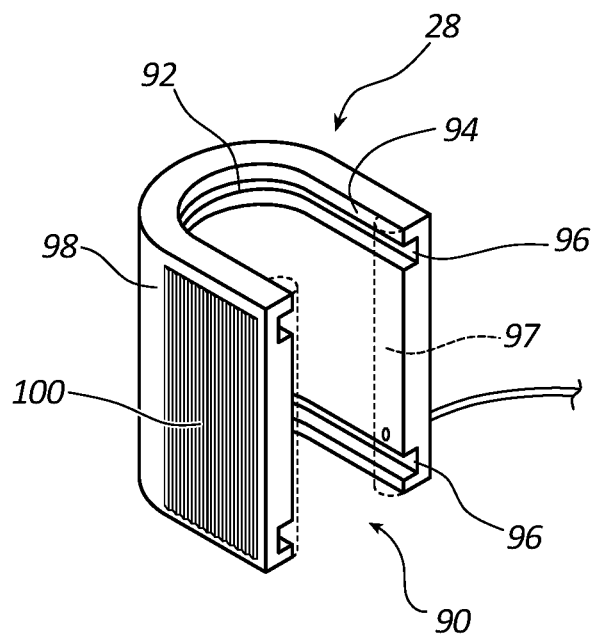
FIG. 7 illustrates an isometric view of a locking member of the tissue opening closure device of FIG. 1

In addition to the biasing member 30 controlling movement of the needle actuation handle 20 relative to the proximal handle 18, the lock member 28 prevents the inadvertent distal movement before actuation. As illustrated in FIGS. 6 and 7, the lock member 28 at least partially surrounds the biasing member 30 and the body portion 78 of the needle actuation handle 30 and receives lipped structures 44, such as flanges or ledges, extending from the handle portion 76 and the proximal housing 18. Those lipped structures 44 are received within complementary grooves 96 formed within a channel 90 having a curved surface 92 and generally planar surfaces 94. The locking member 28 prevents the biased movement of the handle portion 76 relative to the proximal housing 18 under the force of the biasing member 30 as the lipped structures 44 slide into the grooves 96 as the locking member 28 is advanced transversely to a longitudinal axis of the proximal housing 18 and the needle actuation handle 20. The lipped structures 44 can extend around the body portion 78 and the opening 82 of proximal housing 18 in a circumferential direction as a continuous lipped structure or can include one or more discrete spaced apart lipped structures.

While reference is made to including the lipped structures on the locking member 28, it will be understood that the locking member can included other structures that capture or engage with the proximal hosing 18 and the needle actuation handle 20. For instance, optionally, extending from the planar surfaces 94 are detents 97 that provide frictional engagement with one or both of the biasing member 30 and the body portion 78 of the needle actuation handle 30.

An outer surface 98 of the locking member 28 includes grasping structures 100, such as grooves, slots, or other texturing, to aid with grasping and manipulating the lock member 28 so a user can disengage the lock member 28. While an outer surface 98 generally mirrors the shape of the curved surface 92 and the planar surfaces 94, this need not be the case and the outer surface 98 can have a variety of other shapes or configurations. Additionally, while reference is made to including the grasping structures and detents, it will be understood that one or more of the outer surface 98, the curved surface 92, and generally planar surfaces 94 can include friction enhancing surfaces to aid with grasping by a user or being securely retained against the biasing member 30 and/or the body portion 78.

Figure 8:
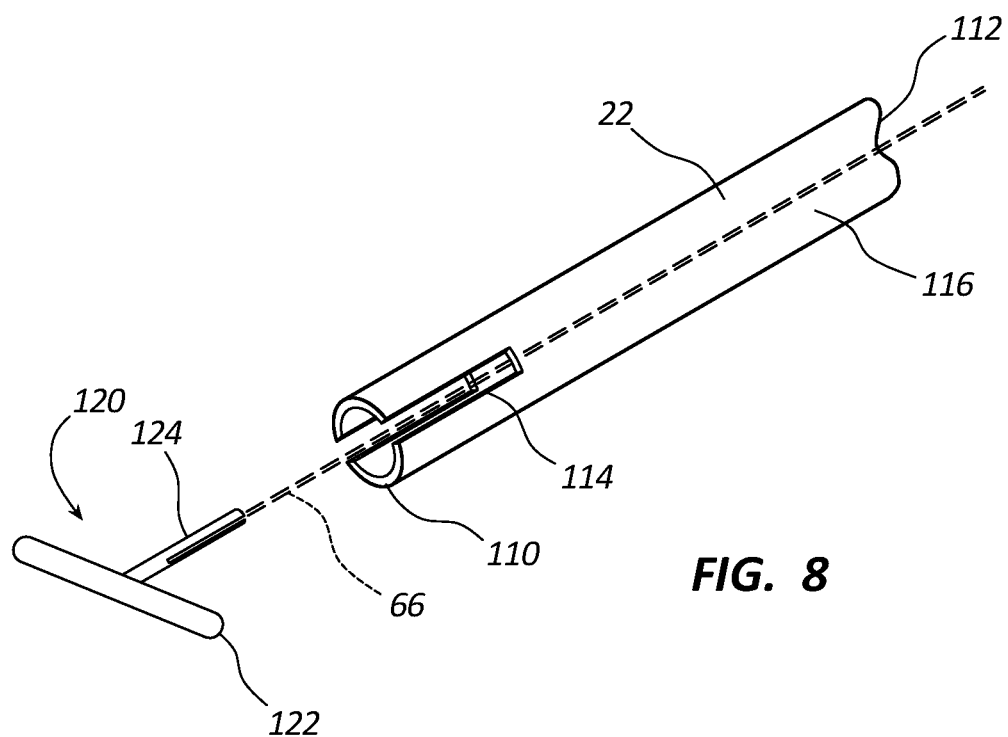
FIG. 8 illustrates a portion of a needle and suture anchor of the tissue opening closure device of FIG. 1.

Returning to FIG. 5, with removal of the lock member 28, the needle actuation handle 20 can move into and from the proximal handle 18, thereby moving the needles 22 through the needle port 32a, 32b to puncture tissue. This movement advances a distal end 110 of each needle 22 and deploys a suture anchor 120 from each needle 22, as illustrated in FIGS. 8-10. The suture anchor 120 is partially retained within a lumen 112 of the needle 22 and partially extends through a slot 114 extending proximally from the distal end 110. The suture 66 attached to each suture anchor 120 extends proximally within the lumen 112 of the needle 22 to which the suture anchor 120 is selective attached. The legs 122 of the suture anchor 120 bend proximally from a base 124, with the legs 122 and the base 124 generally forming a T-shape. The legs 122 can rest, in one configuration, along an outer surface 116 of the needle 22, when the needle 22 is disposed within the needle lumen 34a, 34b. The legs 122 remain in this orientation as the needle 22 is advanced from the needle port 32a, 32b and through the tissue as a sharpened edge 130 of the distal end 110. Once through the tissue, the legs 122 extend outwardly and away from the outer surface 116, as illustrated in FIG. 9, returning to the general T-shape configuration. When the needle actuation handle 20 is moved proximally, frictional engagement of the suture anchor 120 within the lumen 112 and slot 114 is overcome as the suture anchor 120 is brought into contact with the tissue so that the suture anchor 120 is deployed from the retracted needle 22.

The suture anchor 120 illustrated in FIGS. 8-10 can be fabricated from polypropylene or another polymer. The legs 122 can be integrally formed with the base 124 that is subsequently bonded to the suture 66. For instance, the base 124 can include an opening 126 providing access for the suture 66 into a lumen 128. The suture 66 can be secured within the lumen 128, such as through thermal welding, adhesives, crimping, mechanical affixation, or other attachment techniques. Alternatively, the suture 66 and base 124 can be heated to reflow to form a one-piece, optionally monolithic, suture anchor and suture structure. In still another configuration, the legs 122, whether individually or as a bar-like member forming both legs 122 in the illustrated configuration, can be heated to reflow to form a one-piece, optionally monolithic, suture anchor and suture structure, without the base 124. In this other configuration where the suture anchor 120 does not include the base 124, the legs 122 can be secured to the suture 66 through thermal welding, adhesives, crimping, mechanical affixation, or other attachment techniques.

While reference is made to the legs 122 and the base 124 generally forming a T-shape, it will be understood that other orientations are possible. For instance, the legs 122 can form a V-shape, with the V-shape being open in the proximal direction and with or without the base 124 extending from an apex in the open form. In another configuration, the legs 122 can form a U-shape being open in the proximal direction and with or without the base 124 extending from the curved portion of the U-shape. In still another configuration, the suture 66 is tied to the suture anchor 120, such as at an intermediate position of the legs 122 when no base 124 is included. The knot provides a mechanical connection between the suture 66 and the suture anchor 120. To aid with maintaining the knot, it can be thermally set or can be headed to at least partially reflow.

Figure 11:
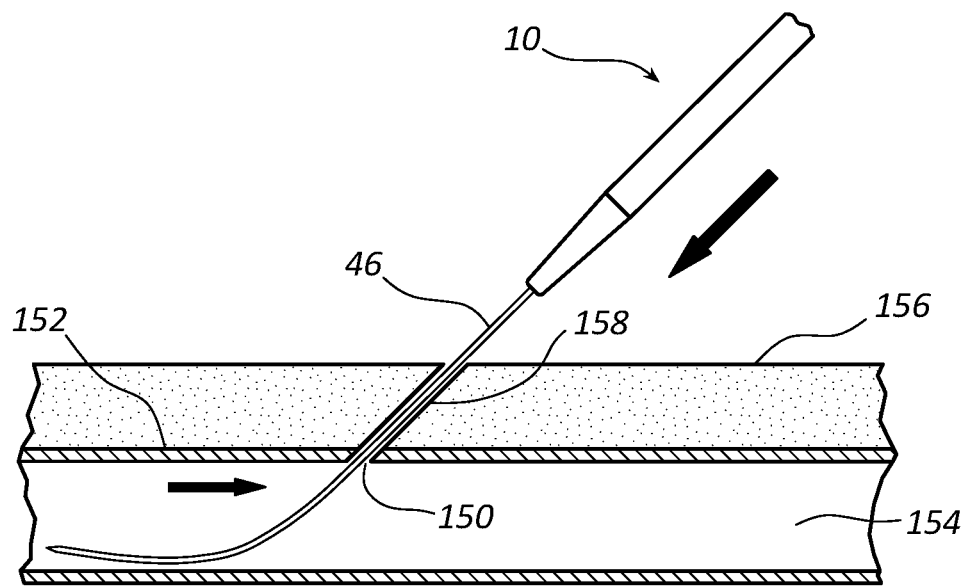
Figure 12:
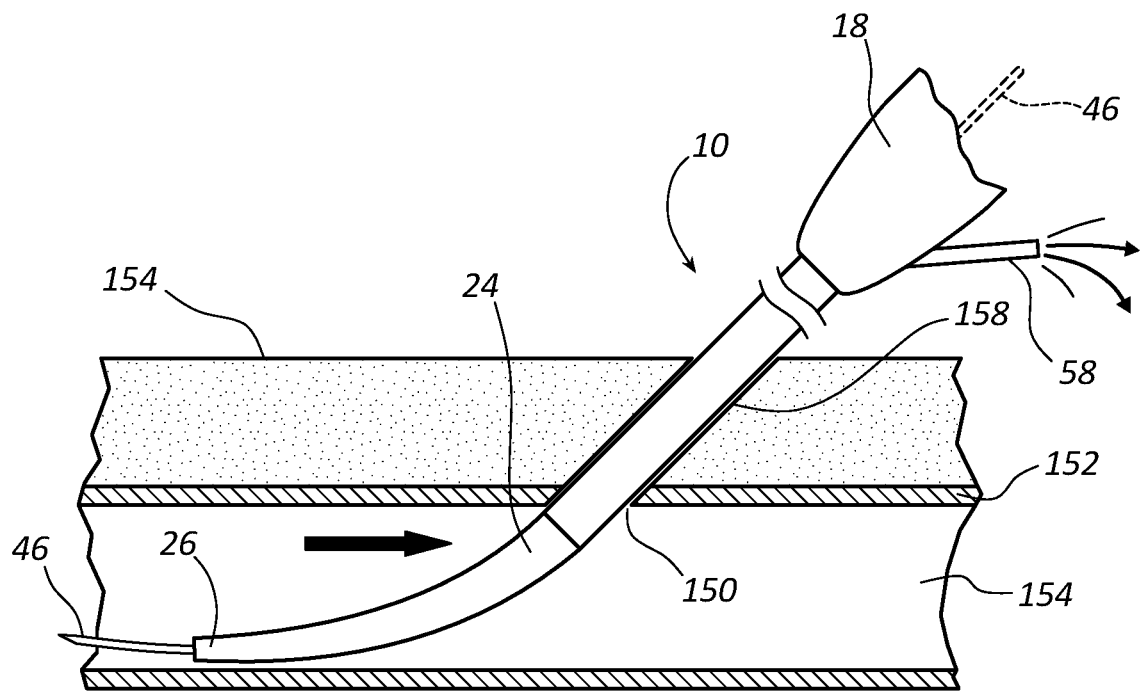

Turning to FIG. 11-21 illustrated is one method for closing a tissue opening or puncture using the closure device of the present invention. FIG. 11 illustrates first steps of a method for closing a puncture 150 in a body wall 152. The method can begin following positioning a guidewire 46 through the skin 156 along the tissue tract 158 through the puncture 150 in the body wall 152 and into the body lumen 154, such as a vessel. With the guidewire 46 in place, the guidebody 24 is advanced over the guidewire 46, as illustrated in FIG. 11, until the guidebody 24 is within the body lumen 154. The guidebody 24 is then retracted proximally until pulsating flow from the outlet port 58 indicates that the shaft 12 is appropriately positioned in the body lumen 154, as illustrated in FIG. 12.

Figure 13:
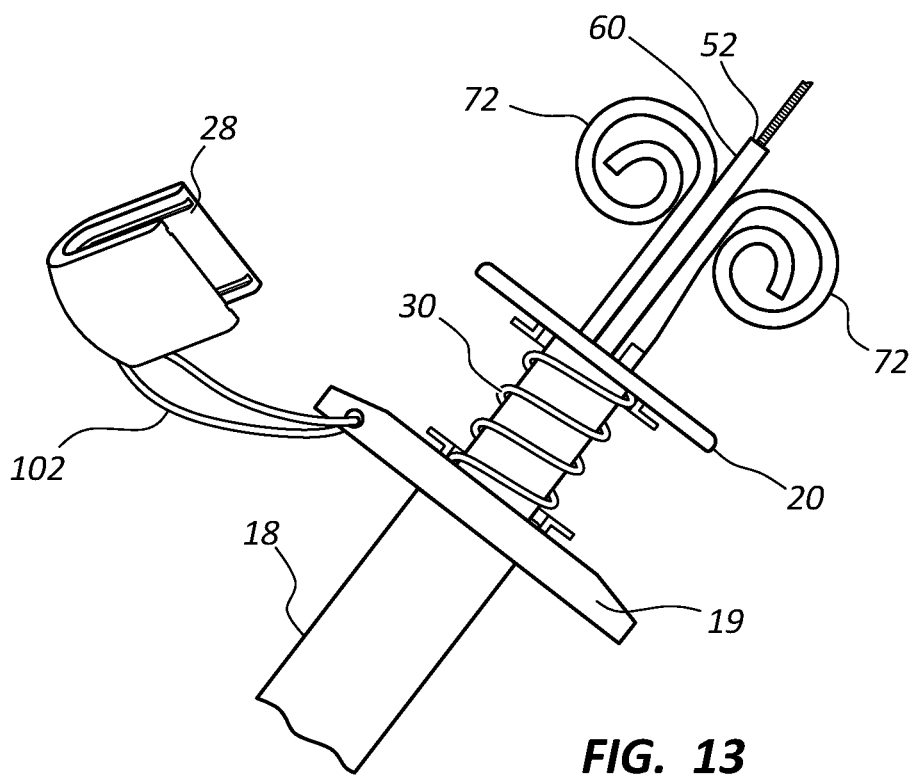
Figure 14:
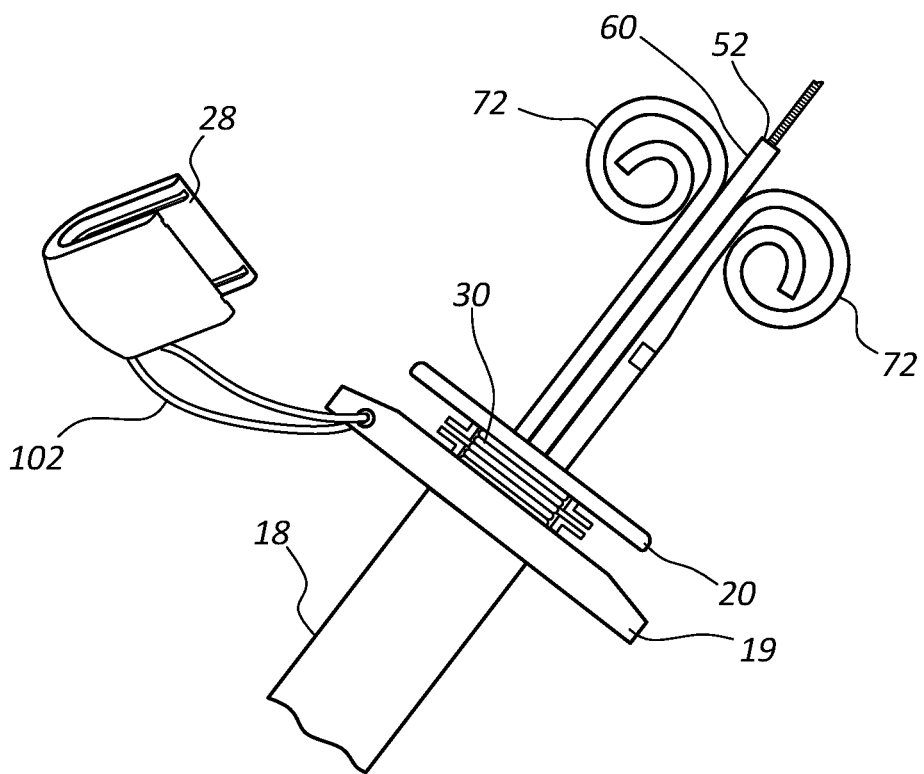
Figure 15:
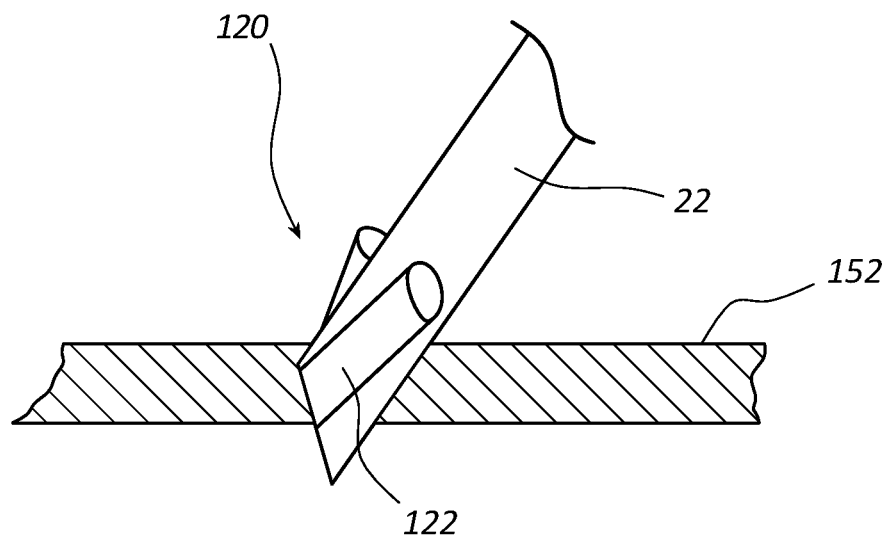

Following positioning the shaft 12 within the body lumen 154, the lock member 28 is disconnected from its engagement with the needle assembly 70. More specifically, a user grasps the outer surface 98 and applies sufficient force to overcome the engagement between the detents 96 and the biasing member 30 and/or the body portion 78. The lock member 28 remains attached to the finger grips 19 of the proximal handle 18 through the tether 102, as illustrated in FIG. 13, but no longer prevents inadvertent movement of the needle actuation handle 20. Instead, the user can advance the needle actuation handle 20 to begin to advance the needles 22 from the needle ports 32*a*, 32*b* so that the legs 122 extend generally transversely or perpendicularly to the suture in a pre-deployed or partially deployed state. The needles 22 can then be advanced into and through the tissue, as illustrated in FIGS. 14 and 15.

Figure 16:
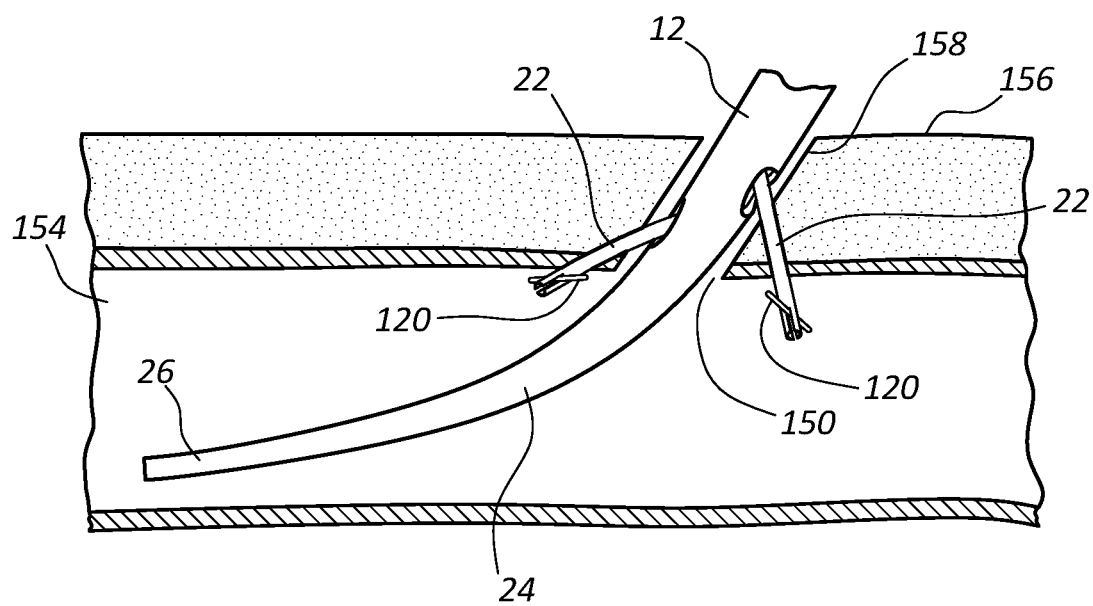

The legs 122 resiliently flex or deflect to extend proximally as the needle 22 penetrates and passes through the body wall 152 on opposite sides of the puncture 150 and into the body lumen 154. Once in the body lumen 154, as illustrated in FIG. 16, the legs 122 extend outwardly from the needle 22 and the suture anchor 120 moves to the deployed state with the legs 122. The legs 122 extend generally transversely or perpendicularly to the suture as the force on the legs 122 as they move through the tissue is released and the resiliency of the material forming the legs 122 allows the legs to transition to the deployed state. Alternatively, the legs 122 can be biased toward the deployed state, such as through forming the legs 122 with or including a biasing member in the legs formed of NITINOL or other shape memory or superelastic material. Alternatively, the legs 122 can be formed of Magnesium or some other biodegradable or bioabsorbable material.

As shown, the suture anchor 120 in the expanded state has a diameter or width greater than the width of the needle 22 or the opening in the body wall 152 formed by the needle 22. This increased dimension prevents passage of the suture anchor 120 when the user pulls back on the needle actuation handle 20 and the legs 122 contact the body wall 152, as illustrated in FIGS. 17-19. Instead, following the initial contact with the body wall 152, continued proximal movement of the needle actuation handle 20 overcomes frictional engagement between the suture anchor 120 and the slot 114, walls of the needle 22, and/or interior surface of the lumen 112 to release or allow detachment of the suture anchor 120 from the needle 22.

Figure 20:
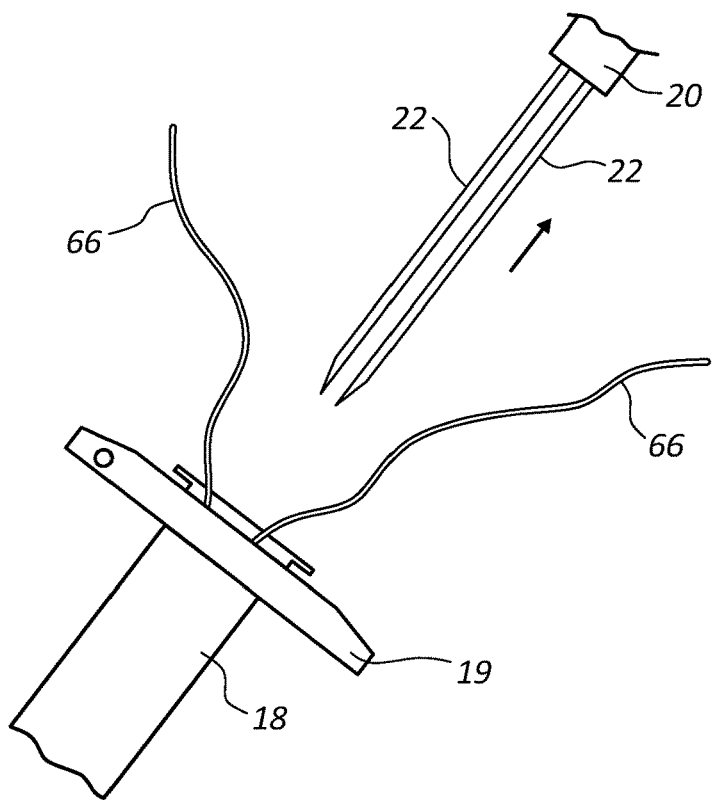
Figure 21:
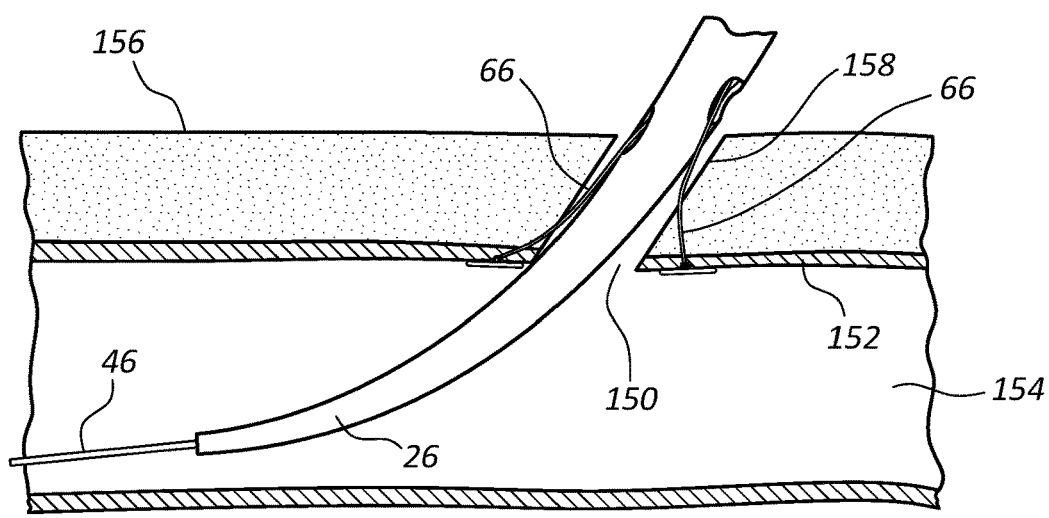

Referring now to FIG. 20, the needle assembly 70 is moved proximally through the shaft 12 and separated from the proximal handle 18. This movement also draws the sutures 66 from within suture storage receptacle 72 leaving the sutures 66 extending from the suture anchor 120 through the shaft 12 and the proximal handle 18, as illustrated in FIGS. 20 and 21. Thereafter, the closure device 10 can be removed while leaving the guidewire 46 in place to retain access to the puncture 150. The sutures 66 from each suture anchor 120 can be tied together to create hemostasis and then the ends of the sutures 66 can be cut following confirmation of hemostasis. This can be achieved directly by the clinician, surgeon, or the like, manually forming, advancing the knot to the puncture 150, and then cutting the suture 66. Alternatively, the clinician, surgeon, or the like can use a knot pusher and suture cutter, such as the suture trimmer disclosed in U.S. Pat. No. 8,211,123 entitled Suture Trimmer and the snared suture trimmer disclosed in U.S. Pat. No. 6,746,457 entitled Snared Suture Trimer, the disclosures of which are is incorporated here by this reference.

Instead of using a knot pusher and suture cutter, the present invention also contemplates use of a knot replacement device that holds sutures in a position to induce hemostasis without the sutures being tied into a knot. The knot replacement device uses a suture lock as a mechanical structure to prevent suture slippage following tensioning to cause hemostasis. This provides for a quick and efficient mechanism to retain the sutures to maintain hemostasis.

Figure 22:
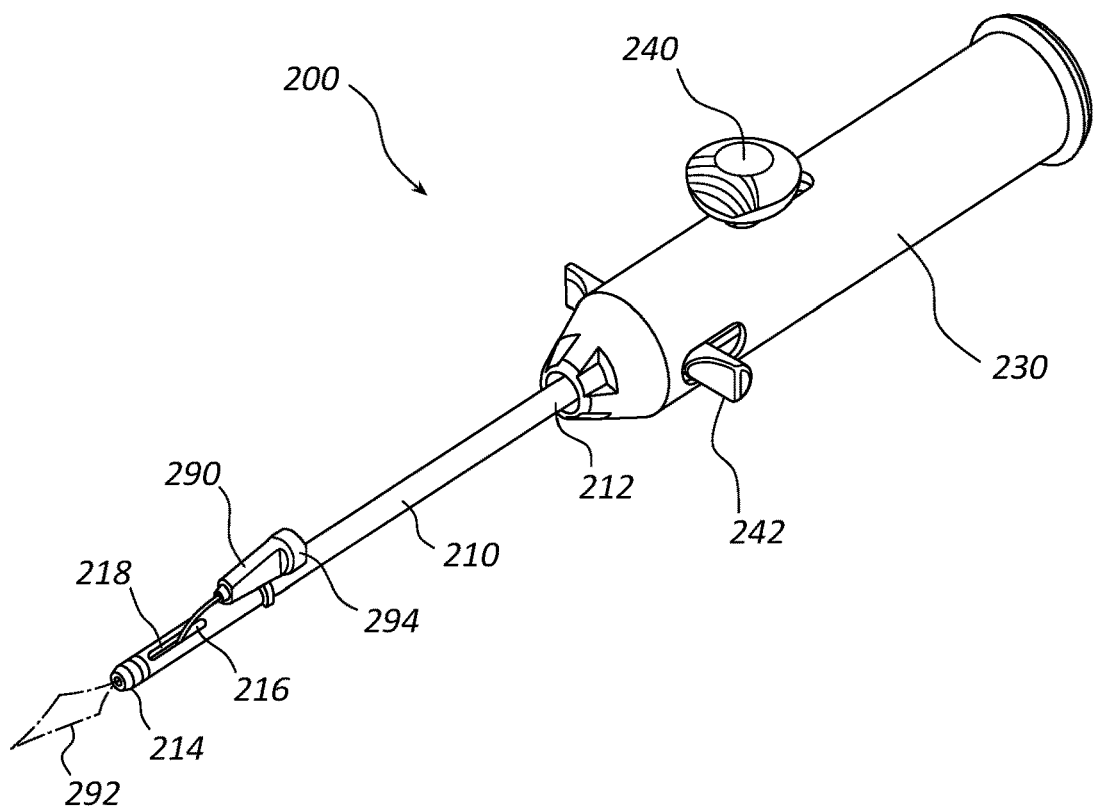
FIG. 22 is an isometric view of a suture trimmer and knot replacement device in accordance with an embodiment of the present invention.
Figure 23:
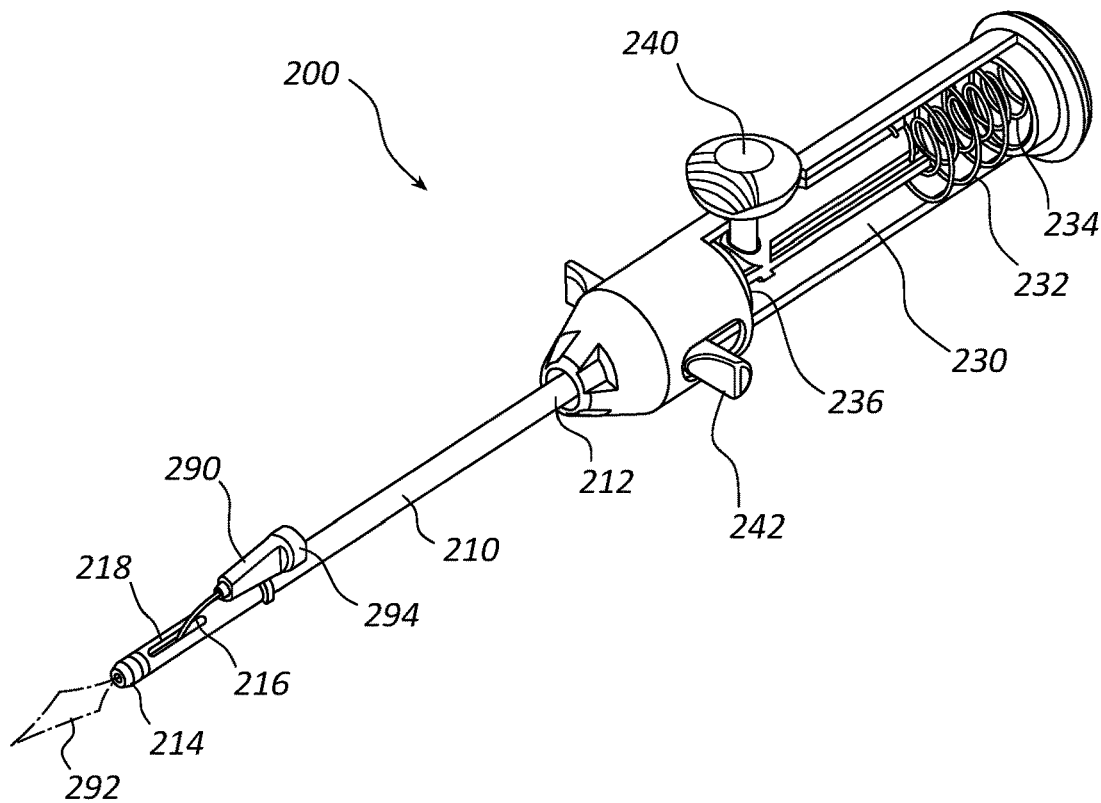
FIG. 23 is a partial cut-away isometric view of a suture trimmer and knot replacement device in accordance with an embodiment of the present invention.
Figure 24:
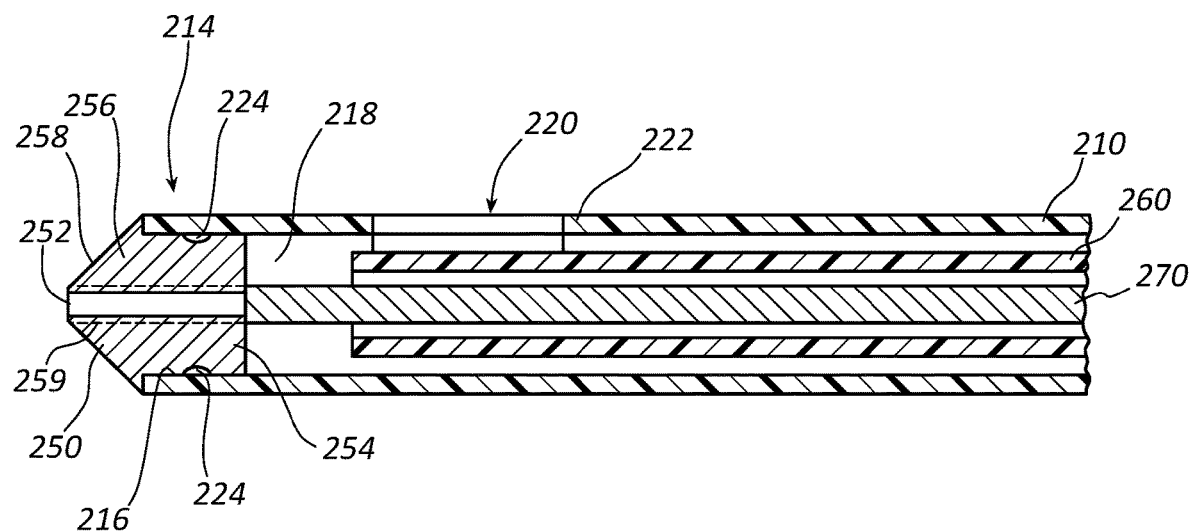
FIG. 24 is a cross-sectional view of a portion of the suture trimmer and knot replacement device of FIG. 22.

Referring now to FIGS. 22-24 there is shown an exemplary embodiment of a knot replacement device 200 in accordance with the present invention. The knot replacement device 200 comprises a shaft 210 having a proximal end 212 and distal end 214, with a handle 230 disposed at the proximal end 212 of the shaft 210. A suture lock 250 is disposed at the distal end 214 within an opening 216 communicating with a bore 218 of the shaft 210. A cutting member 260 and an actuator member 270 are slidably disposed within the bore 218 of the shaft 210, with the cutting member 260 selectively closing an aperture 220 in a wall 222 of the shaft. The cutting member 260 is adapted to cut the sutures 66, while the actuator 270 can aid with deployment of the suture lock 250 from the shaft 210.

Generally, the knot replacement device 200 in accordance with the present invention is suitable for use in remote procedures performed through percutaneous tissue punctures, such as vascular closures, laparoscopic and other minimally invasive procedures and the like. Thus, the shaft 210 of the knot replacement device 200 may be embodied in many lengths to accommodate the various procedures for which the device may be utilized. The diameter of the shaft 210 will be sufficiently small to facilitate the introduction through access sheaths, trocars, and the like, as well as punctures through the tissue of a patient's body, herein referred to as a "tissue tract," and/or coated with lubricious coatings such, as hydrophilic or hydrophobic coatings. Typically, the diameter of the shaft 210 will range from about 4 French to about 10 French, more preferably the diameter of the shaft may range from about 6 French to about 8 French.

It shall be appreciated that although the knot replacement device 200 will be described as being utilized in minimally invasive procedures, it is contemplated that the knot replacement device 200 can be utilized for many open procedures that utilize sutures to close vessels or wounds.

The shaft 210 of the knot replacement device 200 in accordance with the present invention is preferably rigid, typically being formed from of a bio-compatible material such as metal or plastic. Suitable metals include stainless steel, gold plated metals, silver plated metals, platinum or platinum plated metals, or titanium. It shall be understood that other metals may be utilized if an appropriate bio-compatible coated was applied thereto. Suitable plastics include polycarbonate, polyvinyl chloride (PVC), nylon, or similar plastics. As will be described in greater detail below, the shaft 210 may be formed of more than one component. It is further contemplated that the shaft 210 may be constructed to provide a degree of flexibility which will enable the device to be utilized in a greater number of surgical procedures.

The housing 230 may be constructed of a bio-compatible material such as metal or plastic. Suitable metals include stainless steel, gold plated metals, silver plated metals, platinum or platinum plated metals, or titanium. It shall be understood that other metals may be utilized if an appropriate bio-compatible coated was applied thereto. Suitable plastics include polycarbonate, polyvinyl chloride (PVC), nylon, or similar plastics. In a preferred embodiment the housing is constructed of plastic.

In a preferred embodiment the suture lock 250 will be provided within the bore 218 at the distal end 214 of the shaft 210. The suture lock 250 is preferably formed of a material that can firmly engage the sutures and prevent inadvertent slippage that would prevent hemostasis, while also being bio-compatible. For instance, the suture lock 250 is constructed from the following or compounds of the following: polylactic acid (PLA), polyglycolic acid (PGA), polyglactin, polyepsilon-caprolactone, polydioxanone (PDS), polyorthoester, and polyethylene oxide. A cross-section of the suture lock 250 can be rounded, elliptical, oval, polygonal, non-circular or non-rounded, or combinations thereof.

As illustrated in FIG. 24, the suture lock 250 has an opening 252 extending through a proximal portion 254 and a distal portion 256. The proximal portion 254 has a shape complementary to the opening 216. For instance, in the illustrated configuration, the proximal portion 254 has a generally cylindrical form. In contrast, the distal portion 256 has a slightly convex or concave front face 258. The suture lock 250 preferably has a diameter equal to or less than the diameter of the shaft 210 for one or both of the proximal portion 254 and the distal portion 256. In some circumstances, however, a distal end of the suture lock 250 can have a larger diameter than the shaft 210. The suture lock 250 will further include the opening 252 formed through an axis thereof and in communication with the opening 216 formed the shaft 210. The opening 252 also is in communication with the aperture 220 in the wall 222 and has sufficient clearance so that the free ends and limbs of S and S' of the suture 66 may be drawn through the opening 252 and the aperture 220 through the use of a suture snare 290 (FIGS. 22-23). The free ends and limbs S and S' of the suture 66 extend from the aperture 220 in the shaft 210 and enable the tensioning of the suture 66, if needed.

The opening 252 can have a diameter that approximates and accommodates for any suture extrusion dimensional variation to assure interference when the suture is wrapped. The opening 252 can include one or more internal grooves 259 that extend from the proximal portion 254 to the distal portion 256 axially, non-axially, spirally, helically, or combinations thereof. The grooves 259 allow for excess suture to be wedged during lock advancement. The grooves 259 can have uniform or non-uniform depth along the groove's length. For instance, the non-uniformity can be gradual between the proximal portion 254 to the distal portion 256 or can be discontinuous, irregular, or intermittent along the groove's length. Alternate examples of the openings of the suture lock 250 are illustrated in FIGS. 32-36.

The suture lock 250 may be retained within a bore 218 of the shaft 210 through the use of mechanical fasteners or suitable adhesives while being selectively released from the shaft 220. As illustrated in FIG. 24, the detents 224 can be formed on the shaft 210 to hold the suture lock 250. Alternatively, the shaft 210 can be crimped or deformed to form the detents 224 either before or after the suture lock 250 is disposed within the opening 216. The detents 224 provide some resistance to twisting or rotating of the suture lock 250 relative to the distal end 214 of the shaft 210, in addition to limiting longitudinal movement. By so doing, the suture lock 250 does not inadvertently release from distal end engagement while the sutures 66 are twisted or braided together.

It will be understood that while reference is made to inclusion of detents, the shaft and suture lock can have various other configurations. For instance, the suture lock can include a circumferential groove or independent holes or apertures that cooperate with a detent. In still another configuration, the shaft can have a proximally tapering end that receives a proximal portion of the suture lock having sufficient pliability or deformability to being inserted through the opening into the tapering end and be retained therein until released.

With reference to FIGS. 22-24, the cutting member 260 and the actuator 270 may be retained within the bore 218 of the shaft 210 coaxially, though it is contemplated that they may be retained in other manners, such as, side-by-side or offset. Both the cutting member 260 and the actuator 270 are slidably disposed within the bore 218 of the shaft 210 and can be actuated by a first lever 240 and second lever 242 extending from the handle 230. The first lever 240 and second lever 242 are operatively associated with the cutting member 260 and the actuator member 270.

Figure 25:
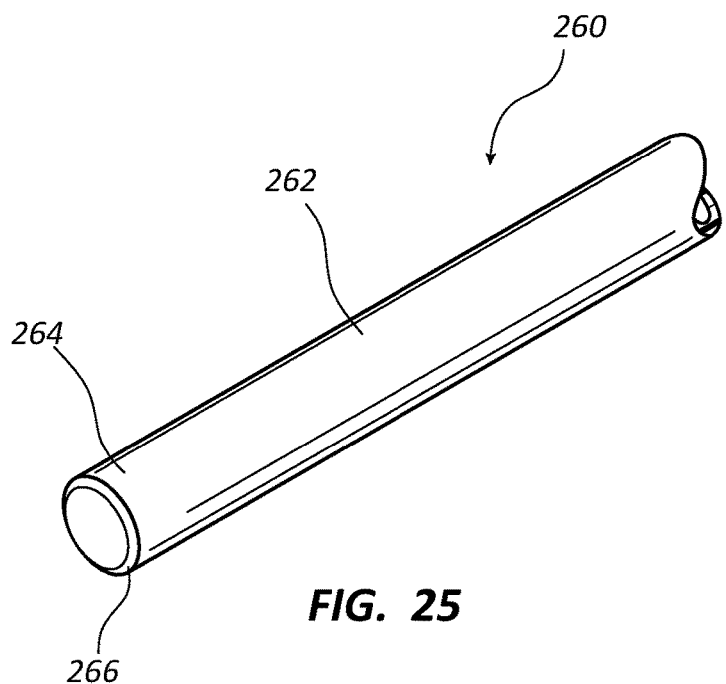
FIG. 25 is an isometric view of a cutting member of the suture trimmer and knot replacement device of FIG. 22.

As shown in FIG. 25, the cutting member 260 comprises an elongated member 262 having a proximal end and a distal end 264. A cutting edge 266 is formed within the cutting member 260 adjacent to the distal end 264. The second lever 242 is coupled to the cutting member 260 adjacent to the proximal end. The lever 242 is further configured to engage a biasing member 232, such as a spring, within the handle 230, as shown in FIG. 23.

The cutting member 260 may be constructed of a bio-compatible material, such that the material chosen is capable of having a sufficiently sharp cutting edge 264 formed therein. For example, surgical stainless steel may be utilized as well as titanium. Furthermore, it is contemplated that the cutting member 260 may include one or more elements coupled together. For example, the elongated member 262 of the cutting member 260 may be constructed of a bio-compatible material such as plastic and the sharp cutting edge 264 may be formed of metal, the cutting edge 264 being mounted to the elongated member 262 to form a single structure.

The actuator 270 may be constructed of a bio-compatible material such as metal or plastic. In a preferred embodiment the actuator 270 is constructed of a bio-compatible plastic. Additionally, the actuator 270 may be constructed of multiple pieces, wherein the actuator 270 and lever are assembled utilizing known methods of mechanical fastening or through the use of an adhesive. It is further contemplated that the actuator 270 and lever may be integrally formed or a one-piece construction, such as through the use of injection molding.

Figure 26:
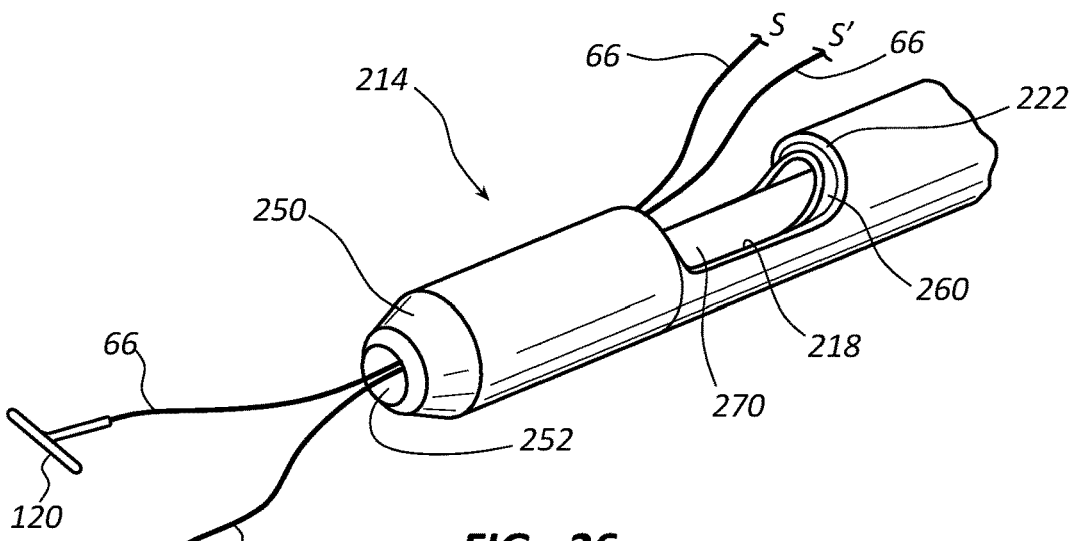
FIG. 26 is a partial isometric view of the distal tip of the suture trimmer and knot replacement device in accordance with the present invention illustrating sutures disposed therethrough and the suture retainer is in a retracted position.
Figure 27:
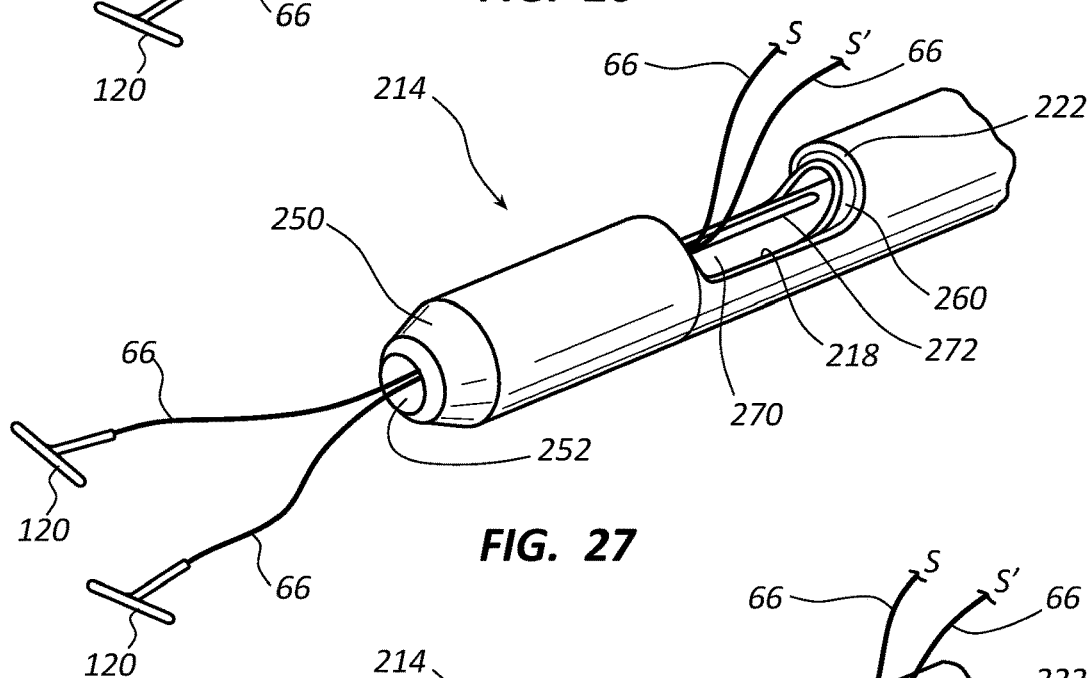
FIG. 27 is a partial isometric view of the distal tip of the suture trimmer and knot replacement device in accordance with the present invention illustrating sutures being disposed therethrough wherein the suture retainer is in a deployed position.
Figure 28:
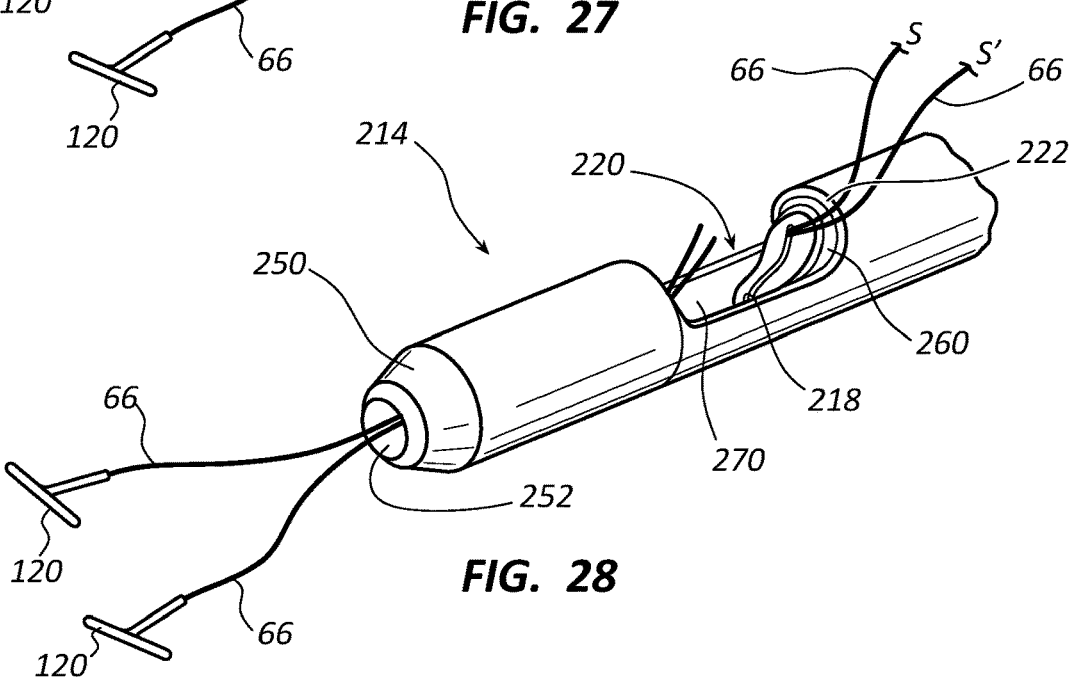
FIG. 28 is a partial isometric view of the distal tip of the suture trimmer and knot replacement device in accordance with the present invention illustrating sutures being disposed therethrough wherein the cutting member has been activated.

Referring now to FIGS. 26-28 there is shown a distal end of the knot replacement device 200 in accordance with the present invention in use. As shown, the sutures 66 have the two free ends, S and S,' those two ends S and S' having been pulled through the suture lock 250 by the suture snare 290. For instance, following placing the two free ends S and S' of the suture 66 within a distal end portion 292 of the suture snare 290 that has been disposed through the opening 216, a housing 294 of the suture snare 290 is detached from the shaft 210 (FIG. 23) and removed, thereby allowing a user to draw the distal end portion 292, with the captured suture ends S and S' through the opening 216 and the suture lock 250. As the distal end portion 292 is drawn through opening 218 and from the aperture 220, the free ends S and S' are drawn through to extend from the shaft 210.

With continued reference to FIGS. 26-28, there is shown the distal end of the knot replacement device 200 in accordance with the present invention. FIG. 26 illustrates the actuator 270 retracted to receive the sutures 66 through manipulation of the first lever 240 proximally. When the first lever 240 is released, the biasing member 232 coupled to the proximal end of the actuator 270, causes the actuator 270 to advance distally and partially closing the bore 218 adjacent the aperture 220, as illustrated in FIG. 27. A secondary biasing member 236, such as a spring, distal a distal end of the first lever 240 limits distal movement of the actuator 270 until the suture lock 250 is to be deployed from the shaft 210. The biasing force of the secondary biasing member 236 can be overcome through distal movement of the first lever 240 to distally advance the distal end of the actuator 270 against the proximal portion 254 to release it from, in one example, engagement with the detent 224, or other rotational and/or longitudinal movement limiter.

As shown, the actuator 270 includes a groove 272 within which the sutures 66 can be disposed to protect the sutures 66 from inadvertent cutting by the edges of the aperture 220. If the suture 66 were allowed to contact the edge of the aperture 220, a nick or cut may be formed in the sutures 66, this may lead to failure of the sutures 66 during tensioning and before the suture lock 250 can be placed appropriately. If the sutures were to fail the clinician, surgeon, or the like would be required to place additional sutures. Therefore, the actuator 270 prevents the suture from being cut or abraded by the edge of the aperture 220 which may lead to failure of the suture.

Referring now to FIG. 28, there is shown a partial view of the distal end of the knot replacement device 200 in accordance with the present invention where the cutting member 260 has been actuated to cut the sutures. For instance, with the sutures 66 captured by the actuator 270 the knot replacement device 200 is rotated to tension the sutures and create hemostasis of the puncture. This also braids or twists the sutures 66 together. When the braided or twisted portion is drawing into a lumen 256 of the suture lock 250, sufficient frictional contact with the sutures 66 occurs to prevent suture slippage and releasing of the tensions.

Upon actuation, the cutting edge 264 is advanced from a shielded position within the shaft 210 toward the sutures 66 through manipulating the lever 242. The cutting member 260 is advanced from the shielded position by applying a force to the lever 242, the lever 242 being coupled to the proximal end of the cutting member 260. As described above, the cutting member 260 is actuated by pulling back on the lever 242, thereby advancing the lever 242 towards the proximal end of the knot replacement device 200 and compressing a second biasing member 234 disposed within the handle 230. As shown, the cutting member 260 includes the sharpened cutting edge 266 that cooperates with a distal end of the aperture to shear or cut the sutures 66. As described above and illustrated in FIG. 28, the cutting member 260 of the knot replacement device 200 moves relative to the shaft 210.

Referring now to FIGS. 29-32, there is shown a partial view of the distal end 214 of the knot replacement device 200 in accordance with the present invention disposed in various states of use associated with a method of the present invention.

Figure 29:
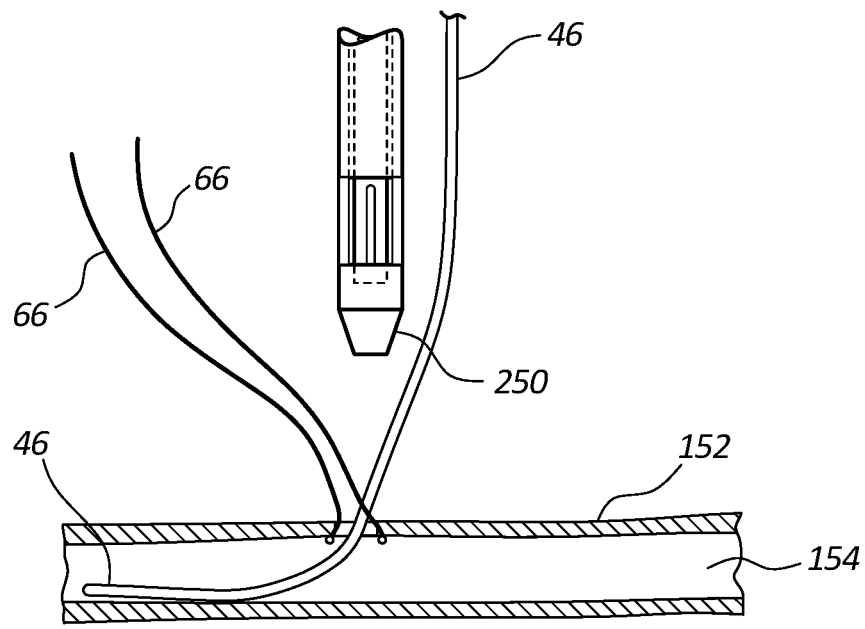
FIG. 29 is a partial view of the distal tip of the suture trimmer and knot replacement device in accordance with the present invention illustrating sutures placed in a patient's tissue.
Figure 30:
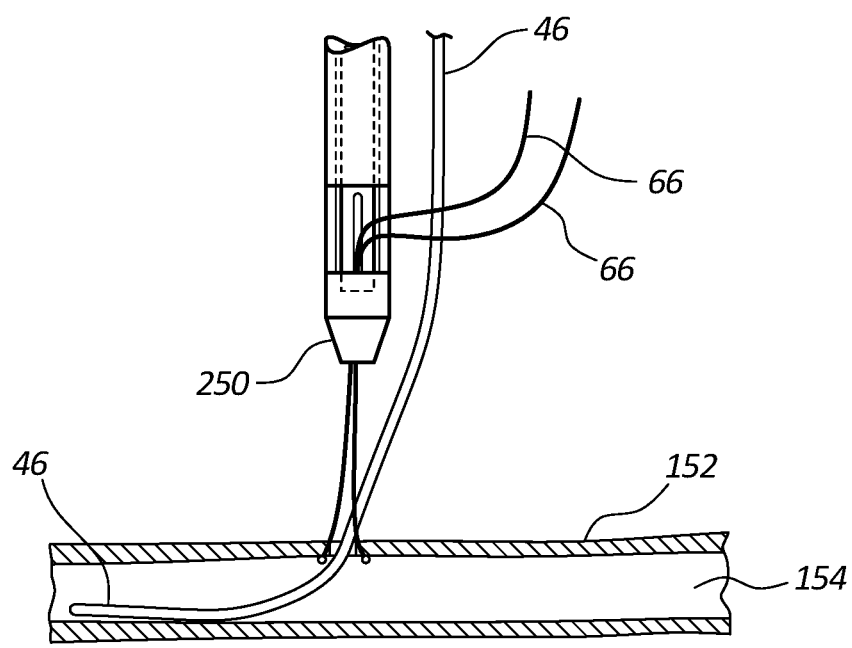
FIG. 30 is a partial view of the distal tip of the suture trimmer and knot replacement device in accordance with the present invention illustrating sutures extending through the distal tip with the suture retainer in a retracted position.
Figure 31:
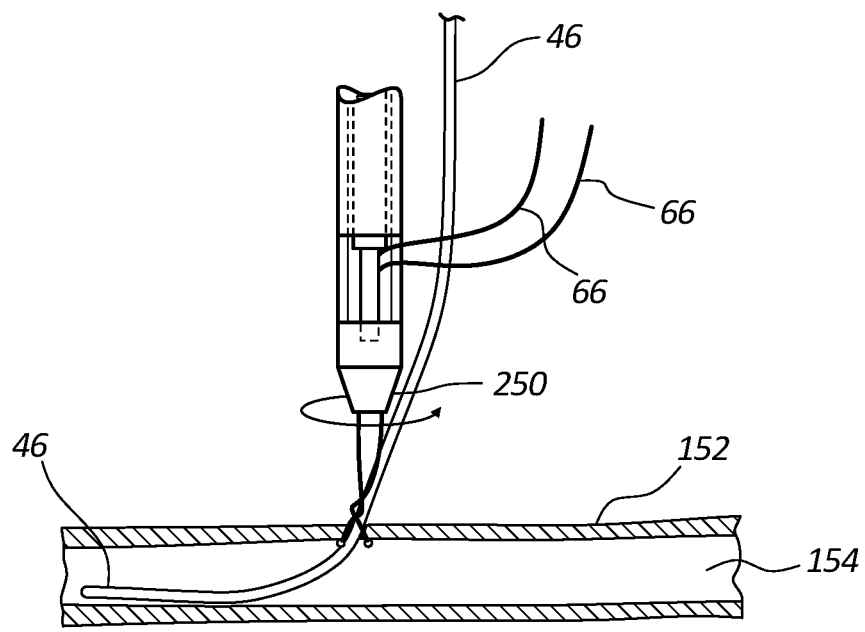
FIG. 31 is a partial view of the distal tip of the suture trimmer and knot replacement device in accordance with the present invention, wherein the suture trimmer and knot replacement device has been rotated to twist the sutures together.

Referring now to FIG. 29, there is shown the distal end of the knot replacement device 200 with the actuator 270 disposed in a distally advanced position. Sutures 66 have been positioned in tissue as shown, wherein the two free ends S and S' of the sutures 66 extend from the tissue. In this position the knot replacement device 200 is ready to receive the sutures 66 when the suture snare 290 (FIG. 22) draws the two free ends S and S' through the lumen 256 of the suture lock 250 and from the aperture 220 in the wall 222, as illustrated in FIG. 30.

Once the sutures 66 are positioned to extend through the aperture 220, the force applied to the first lever 240 (FIG. 22) is released, thereby allowing the actuator 270 to advance distally within the bore 218 of the shaft 210. The distal end of the actuator 270 passes the distal end of the aperture 220 but remains proximal to the proximal portion 254 of the suture lock 250, as illustrated in FIG. 30.

With the sutures 66 locked in position through positioning of the actuator 270, the knot replacement device 200 is rotated to twist or braid the sutures 66 together. This can include one or more full or partial rotations until the sutures 66 have a cross-sectional dimension that is sufficient to frictionally engage with the opening 252. For instance, in one configuration the opening 252 has a diameter that receives two sutures and approximates and accommodates for any suture extrusion dimensional variation to assure interference when the suture is wrapped.

Figure 32:
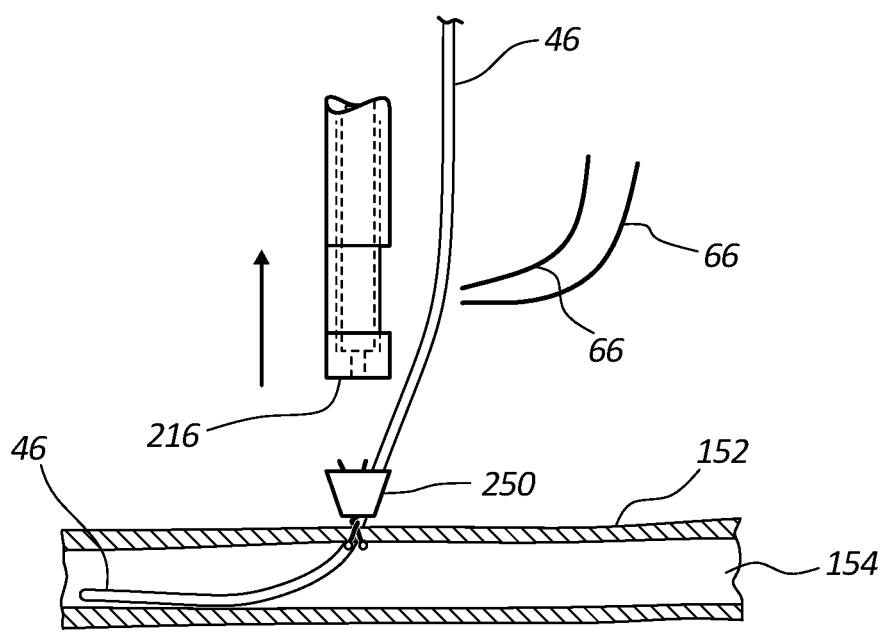
FIG. 32 is a partial view of the distal tip of the suture trimmer and knot replacement device in accordance with the present invention, wherein the sutures have been cut and the suture lock released.

When sufficient twisting or braiding has occurred, an axial force is applied to the second lever 242 to distally advance the cutting member 260 to cut or sever the sutures 66. Additionally, either simultaneously with, or following movement of the cutting member, the first lever 240 is moved distally, overcoming the biasing force of the secondary biasing member 236, so that the distal end of the actuator 270 contacts the proximal portion 254 of the suture lock 250. Continued distal movement, distally advances the suture lock 250 from the distal end 215 of the shaft 210 to overcome the engagement forces between the detent 224 and the suture lock 250, for instance, as illustrated in FIG. 32. The engagement force is less than the anchor suture attachment force, which is about 2 lbf. The engagement force, therefore, is about 0.5 to about 1.25 lbf.

Turning to FIGS. 33-37, illustrated are different configurations of the suture lock according to the present invention. Like reference numerals are associated with like elements. Additionally, the disclosure of the suture lock 250 is applicable to the suture locks illustrated in FIGS. 33-37. For instance, openings in the suture locks of FIGS. 33-37 can have a diameter that approximates and accommodates for any suture extrusion dimensional variation to assure interference when the suture is wrapped. The openings can include internal grooves that extend from the proximal portion to the distal portion axially, non-axially, spirally, helically, or combinations thereof. The grooves allow for excess suture to be wedged during lock advancement. The grooves can have uniform or non-uniform depth along the groove's length, such as gradual or discontinuous, irregular, or intermittent depth non-uniformity between the proximal portion and the distal portion.

With reference to FIG. 33, illustrated is a suture lock 350a having an opening 352a. The opening 352a includes one or more grooves 359a disposed around the periphery of the opening 352a. The grooves 359a include a curved wall 374a extending from an inner wall 376a of the opening 352a in a radial direction, the inner wall 376a forming an inner periphery 378a of the opening 352a and the outer periphery of the curved wall 374a, in the radial direction, forming an outer periphery 380a of the opening 352a.

FIG. 34 illustrates another suture lock 350b having an opening 352b. The opening 352b includes one or more grooves 359b disposed around the periphery of the opening 352b. The grooves 359b includes a wall 374b extending from an inner wall 376b of the opening 352b in the radial direction, the inner wall 376b forming an inner periphery 378*b* of the opening 352*b* and an apex of the wall 374*b* forming an outer periphery 380*b* of the opening 352*b*.

FIG. 35 illustrates another suture lock 350*c* having an opening 352*c*. The opening 352*c* includes one or more grooves 359*c* disposed around the periphery of the opening 352*c*. The grooves 359*c* includes a curved wall 374*c* extending radially inwardly from an outer wall 376*c* of the opening 352*c*, the innermost periphery of the curved wall 374*c* forming an inner periphery 378*c* of the opening 352*b* and the outer wall 376*c* forming an outer periphery 380*c* of the opening 352*c*.

FIG. 36 illustrates another suture lock 350*d* having an opening 352*d*. The suture lock 350*d* is similar to suture lock 350*a*, however, the grooves 359*d* have differing depths in a radial direction and differing width in a circumferential direction.

FIG. 37 illustrates another suture lock 350*e* having an opening 352*e*. The suture lock 350*e* is similar to suture lock 350*a*, however, the opening 352*e* is non-circular in that the opening 352*e* has a long axis 382*e* and a short axis 384*e* such that the opening 352*e* approximate an oblong or rectangular shape with the grooves 359*e*. While reference is made to approximating an oblong or rectangular shape, the opening can have other polygonal, elliptical, or other non-polygonal shapes so long as there is a long axis and a short axis, even if there is no symmetry about one or both of the long axis and the short axis.

It is understood that any of the structures and features of embodiments illustrated in FIGS. 33-37 can be combined into a single suture lock. Generally, each suture lock can include an opening and grooves, with such opening approximating any polygonal, elliptical, or other non-polygonal shape and such grooves having the same or different depths, widths, and shapes in the suture lock and being uniformly or non-uniformly distributed about the periphery of the suture lock.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description, with it being understood that the scope of the present disclosure extends to rewriting any of the claims to depend from any other claim, to include multiple dependencies from any combination of other claims, and/or to combine multiple claims together. Additionally, elements described in relation to any embodiment depicted and/or described herein may be combinable with elements described in relation to any other embodiment depicted and/or described herein. Such also extends to the embodiments as described in the Summary section, as well as the Detailed Description section, including the drawings. The scope of the present disclosure also extends to inserting and/or removing any combination of features from any claim or described embodiment, for insertion into another claim or embodiment, or drafting of a new claim including any combination of such features from any other claim(s) or embodiments. All changes which come within the meaning and range of equivalency of the claims are to be embraced within their scope.

What is claimed is:

1. A closure device for closing an opening in tissue as part of a closure system, the closure device comprising:
   a needle actuation handle cooperating with a housing;
   a first hollow needle selectively movable by the needle actuation handle, the first hollow needle comprising a slot extending proximally from a distal end of the first hollow needle;
   a suture anchor frictionally engaged with the slot and a lumen of the first hollow needle and coupled to a suture, a portion of the suture anchor that extends transversely to a portion of the suture anchor mounted to the suture resting along sides of an outer surface of the first hollow needle on opposite sides of a longitudinal axis of the first hollow needle as the first hollow needle is advanced through tissue adjacent the opening.

2. The closure device of claim 1, further comprising a locking member selectively disposed about a body of the needle actuation handle distal a handle portion.

3. The closure device of claim 2, wherein the needle actuation handle is biased proximally from the housing.

4. The closure device of claim 3, further comprising a second hollow needle, the first hollow needle begin configured to exit a first port of the housing and the second hollow needle being configured to exit a second port of the housing.

5. The closure device of claim 4, wherein the first port is proximal the second port.

6. The closure device of claim 1, further comprising a shaft extending from the housing, the shaft comprising at least one of a guidewire lumen, a suture lumen, and a marker lumen.

7. The closure device of claim 1, wherein the portion of the suture anchor that extends transversely comprises two legs extending transversely to the suture in the pre-deployed state and a deployed state.

8. A closure system for closing an opening in tissue, the closure system comprising:
   a closure device comprising:
      a housing;
      a needle actuation handle cooperating with the housing;
      a first hollow needle selectively movable by the needle actuation handle, the first hollow needle comprising a slot extending proximally from a distal end of the first hollow needle and communicating with a lumen of the first hollow needle that is configured to receive a suture; and
      a suture anchor frictionally engaged with the slot and the lumen of the first hollow needle and coupled to the suture, a portion of the suture anchor that extends transversely to a portion of the suture anchor mounted to the suture resting along sides of an outer surface of the first hollow needle on opposite sides of a longitudinal axis of the first hollow needle as the first hollow needle is advanced through tissue adjacent the opening; and
   a knot replacement device configured to position a suture lock on the suture.

9. The closure system of claim 8, further comprising a suture storage receptacle configured to receive a portion of the suture.

10. The closure system of claim 8, further comprising a locking member selectively disposed about a body of the needle actuation handle distal a handle portion, wherein the locking member slidable cooperates with a portion of the needle actuation handle.

11. The closure system of claim 10, wherein the locking member comprises a groove to accommodate a complementary structure of the needle actuation handle.

12. The closure system of claim 8, wherein the needle actuation handle and the first hollow needle are selectively slidable in both a proximal-to-distal direction and a distal-to-proximal direction.

13. The closure system of claim 8, with the needle actuation handle and the first hollow needle being selectively removable from the housing.

14. The closure system of claim 8, further comprising a guidewire lumen extending proximally adjacent to a suture storage receptacle configured to receive a portion of the suture.

15. A method comprising:
   positioning a distal end of a closing device through a tissue opening, the closing device comprising a housing from which a first hollow needle is advanceable;
   advancing the first hollow needle from the housing towards tissue adjacent to the tissue opening, the first hollow needle comprising a suture anchor frictionally engaged with a slot and a lumen of the first hollow needle and coupled to a suture, the suture anchor comprising two legs extending transversely to a portion of the suture anchor mounted to the suture; and
   advancing the first hollow needle through the tissue adjacent to the tissue opening, the two legs resting along sides of an outer surface of the first hollow needle on opposite sides of a longitudinal axis of the first hollow needle as the first hollow needle is advanced through tissue adjacent the opening.

16. The method of claim 15, further comprising proximally retracting the first hollow needle following advancing the first hollow needle through the tissue to overcome the frictional engagement between the suture anchor and walls of the slot and the lumen.

17. The method of claim 16, further comprising capturing the suture following removable of the closing device with a knot replacement device.

18. The method of claim 17, further comprising twisting the suture.

19. The method of claim 18, following twisting the suture, advancing a suture lock on the suture, the suture lock comprises at least one groove to aid with capturing and securing the suture.

20. The method of claim 19, further comprising cutting the suture.

* * * * *